United States Patent
Kossaczka et al.

(10) Patent No.: US 6,797,275 B1
(45) Date of Patent: Sep. 28, 2004

(54) **METHOD OF IMMUNIZING HUMANS AGAINST *SALMONELLA TYPHI* USING A VI-REPA CONJUGATE VACCINE**

(75) Inventors: Zuzana Kossaczka, Bethesda, MD (US); Shousun Chen Szu, Bethesda, MD (US); John B. Robbins, Chevy Chase, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/653,433

(22) Filed: Sep. 1, 2000

Related U.S. Application Data

(63) Continuation-in-part of application No. PCT/US98/25746, filed on Dec. 4, 1998.

(51) Int. Cl.$^7$ .............................................. A61K 39/112
(52) U.S. Cl. ............................... 424/258.1; 424/195.11; 424/184.1; 424/197.1; 424/236.1; 424/192.1; 536/123; 528/332
(58) Field of Search ........................ 424/258.1, 195.11, 424/184.1, 197.1, 236.1, 192.1; 536/123; 528/332; 530/402

(56) References Cited

U.S. PATENT DOCUMENTS

| | | | | |
|---|---|---|---|---|
| 5,204,098 A | * | 4/1993 | Szu et al. | 424/92 |
| 5,738,855 A | * | 4/1998 | Szu et al. | 424/258.1 |
| 5,952,454 A | * | 9/1999 | Kovac et al. | 528/332 |
| 6,309,646 B1 | * | 10/2001 | Lees | 424/195.11 |

OTHER PUBLICATIONS

Szu, SC et al, APSTS, 3rd, Dec. 8, 1997, abstract S7–1, p. 50.*
Fattom, A et al, Infection and Immunity, Feb. 1992, vol. 60(2), pp. 584–589.*
Szu, Shousun C. et al., "Laboratory and Preliminary Clinical Characterization of Vi Capsular Polysaccharide–Protein Conjugate Vaccines", Infection and Immunity, 62:4440–4444 (Oct. 1994).
Kossaczka, Zuzana et al., "Synthesis and Immunological Properties of Vi and Di–O–Acetyl Pectin Protein Conjugates with Adipic Acid Dihydrazide as the Linker", Infection and Immunity, 65:2088–2093 (Jun. 1997).
Fattom, A. et al., "Comparative Immunogenicity of Conjugates Composed of the *Staphylococcus aureus* Type 8 Capsular Polysaccharide Bound to Carrier Proteins by Adipic Acid Dihydrazide or N–Succinimidyl–3–(2–Pyridyldithio)propionate", Infection and Immunity, 60:584–589 (Feb. 1992).
Szu et al., "Phase II Trials of Conjugates of *S. Typhi* Vi and of *S. Paratyphi* A O–Specific Polysaccharide (O–SP) Conjugates in Doing Thap Province, Vietnam", Abstract S7–1 form the Abstract Book of the "Third Asia–Pacific Symposium on Typhoid Fever and Other Salmonellosis," hosted by the Indonesian Society for Microbiology, Denpasar, Bali–Indonesia, Dec. 8–10, 1997.
Kossaczka, S., et al., "Safety and Immunogenicity of Vi Conjugate Vaccines for Typhoid Fever in Adults, Teenagers, and 2– to 4–Year–Old Children in Vietnam", Infection and Immunity, 67:5806–5810 (Nov. 1999) (published after the Dec. 4, 1998 priority date).
Copy of International Search Report from PCT/US98/25746.

* cited by examiner

*Primary Examiner*—Lynette R. F. Smith
*Assistant Examiner*—Ginny Allen Portner
(74) *Attorney, Agent, or Firm*—Klarquist Sparkman, LLP

(57) ABSTRACT

This invention relates to conjugates of the Vi polysaccharide of *S. typhi* with the carrier *Pseudomonas aeruginosa* recombinant exoprotein A (rEPA), and compositions thereof, and to methods of using of these conjugates and/or compositions thereof for eliciting an immunogenic response in humans, including responses which provide protection against, or reduce the severity of, *S. typhi* bacterial infections. The conjugates, and compositions thereof, are useful as vaccines to induce serum antibodies againt *S. typhi* and are useful to prevent and/or treat illnesses caused by *S. typhi*.

19 Claims, No Drawings

METHOD OF IMMUNIZING HUMANS AGAINST *SALMONELLA TYPHI* USING A VI-REPA CONJUGATE VACCINE

This application is a continuation-in-part of PCT International Application No. PCT/US98/25746, filed on Dec. 4, 1998.

FIELD OF THE INVENTION

This invention relates to methods of using conjugates of the capsular polysaccharide of *Salmonella typhi*, Vi, bound to the carrier *Pseudomonas aeruginosa* recombinant exoprotein A (rEPA) with a carboxylic acid dihydrazide linker, preferably an adipic acid dihydrazide (ADH) linker, and compositions of these conjugates, for eliciting serum antibody responses in humans, including responses which provide protection against, or reduce the severity of, *S. typhi* bacterial infections. The conjugates, and compositions thereof, are useful as vaccines to induce serum antibodies which are useful to prevent and/or treat illnesses caused by *S. typhi*.

BACKGROUND

In developing countries, typhoid fever is common, serious, and increasingly difficult to treat because of resistance of the bacillus to antibiotics. [24, 63–66]. For example, more than 80% of *Salmonella typhi* from the Mekong Delta region of Vietnam are resistant to chloramphenicol and to ampicillin and even more expensive antibiotics such as ciprofloxacin. Typhoid fever has been thought of as a disease of mostly older children and young adults. In children less than 5 years of age, typhoid fever was often unrecognized due to atypical clinical symptoms, difficulties in drawing blood and less-than-optimal culture media. [66–69]. Similar to recent findings in other parts of Southeast Asia [70–72], a preliminary survey in 3 communes of the Dong Thap province of Vietnam showed that the annual attack rate of typhoid fever was highest among children less than 15 years of age: it was 413/100,000 in this age group and 358/100,000 for 2 to 4 year-olds. [73].

Unfortunately, it is unlikely that safe drinking water and foodstuffs will be available in many developing countries, especially in rural areas, in the near future. [24, 66, 74]. Control of typhoid fever by routine vaccination, especially in countries that endure high endemic rates of typhoid fever, has not been adopted because of the limitations of the three licensed vaccines (parenteral inactivated cellular vaccines, oral attenuated *S. typhi* Ty21a, and parenteral Vi polysaccharide). These vaccines confer only approximately 70% immunity to older children and adults but do not protect young children. [24, 1, 30, 75, 76].

Orally administered attenuated *S. typhi* Ty21a requires at least 3 doses, has a low rate of efficacy in areas with a high rate of typhoid fever and in travelers from developed countries and is not immunogenic in young children. Neither the protective antigens nor the vaccine-induced host immune responses have been identified which hinders improvement of the Ty21a vaccine.

Although effective in areas with high rates of typhoid fever, killed whole cell parenteral vaccines elicit a high rate of adverse reactions and have not been shown to be effective in young children. In 1952, Landy concluded that the protective antigen of cellular vaccines is the capsular polysaccharide (Vi) of *S. typhi*.

In two randomized, double-blinded, vaccine-controlled clinical trials, one injection of Vi induced about 70% efficacy in $\geq 5$ year-olds in the Kathmandu Valley of Nepal and in the Eastern Transvaal region of the Republic of South Africa: these regions had a high rate of endemic typhoid (0.4 to 1% per year) [1]. Recently, similar results were obtained by the Lanzhou Institute of Biologic Products in the People's Republic of China [manuscript in preparation]. Vi is easily standardized. The World Health Organization has published requirements for Vi polysaccharide typhoid vaccine and this product is licensed in about 50 countries including the United States [59,60]. But Vi induces only short-lived antibody responses in children two to five years of age and does not elicit protective levels in children less than two years old: in adults, reinjection restores the level of vaccine-induced anti-Vi but does not elicit a booster response. These age-related and T-independent immunologic properties are similar to most other polysaccharide vaccines.

We proposed that it is the vaccine-induced serum IgG anti-Vi that confers immunity. Accordingly, the level of serum IgG anti-Vi should predict the efficacy of Vi vaccine. In order to improve its immunogenicity, Vi was conjugated to proteins using SPDP [51, 52, 54, 62]. The protein carriers for the SPDP linked conjugates included cholera toxin (CT), tetanus toxoid (TT), the B subunit of the heat-labile cholera-like enterotoxin (LT-B) of *Escherichia coli* and the recombinant exoprotein A (rEPA) of *Pseudomonas aeruginosa* (i.e., the nontoxic recombinant form of exotoxin from *Pseudomonas aeruginosa* (ETA) cloned into and secreted by *E. coli*). [Id.]. Recently, we employed another synthesis that treated rEPA with adipic acid dihydrazide (ADH) and bound the hydrazide derivative of rEPA (rEPA-AH) to Vi with 1-ethyl-3-(3-dimethylaminopropyl) carbodiimide (EDC) [31]. The safety and immunogenicity of the Vi-rEPA conjugates prepared either with N-succinimidyl-3-(2-pyridyl dithio) propionate (SPDP, Vi-rEPA$_I$) or adipic acid dihydrazide (ADH, Vi-rEPA$_{II}$) as linkers, were compared sequentially in adults, 5–14 year-olds and then 2–4 year olds in Vietnam. The data set forth in Example 5 herein demonstrate that the resultant conjugate (Vi-rEPA) both enhanced the immunogenicity of and conferred T-cell dependent properties to Vi. Vi-rEPA elicited a booster response in 2 to 4 year-olds with IgG anti-Vi levels approximately 3 times higher than those elicited by Vi in 5 to 14 year-olds. None of the vaccinees had a temperature >38.5° C. or swelling >2.5 cm following injection. On the basis of these results, we initiated a double-blinded placebo-controlled randomized trial to determine the efficacy of Vi-rEPA in 2 to 5 year-old Vietnamese children, an age group for which there is yet no effective typhoid vaccine. The results of that efficacy trial are set forth in Example 6 herein.

BRIEF DESCRIPTION OF THE INVENTION

It is an object of the invention to provide methods of using conjugates of the capsular polysaccharide of *Salmonella typhi* (Vi) bound to the carrier rEPA (as carrier protein) with a carboxylic acid dihydrazide linker, preferably an adipic acid dihydrazide (ADH) linker, and/or compositions thereof, for eliciting an immunogenic response in mammals, including responses which provide protection against, or reduce the severity of, bacterial infections. More particularly, it is an object of the invention to provide methods of using such conjugates, and/or compositions thereof, to induce serum antibodies against the capsular polysaccharide of *S. typhi*, called Vi. The conjugates, and compositions thereof, are useful as vaccines to induce serum antibodies which are useful to prevent typhoid fever.

It is also an object of the invention to provide antibodies which immunoreact with the Vi polysaccharide of *S. typhi* and/or the rEPA carrier, that are induced by these conjugates and/or compositions thereof. Such antibodies may be isolated, or may be provided in the form of serum containing these antibodies.

It is also an object of the invention to provide a method for the treatment or prevention of S. typhi infection in a mammal, by administration of compositions containing the antibodies of the invention, or serum containing the antibodies of the invention.

The invention also provides methods and kits for identifying, detecting, and/or diagnosing S. typhi infection or colonization using the antibodies which immunoreact with the Vi polysaccharide of S. typhi. The invention also relates to methods and kits for identifying, detecting and/or diagnosing the presence of P. aeruginosa and/or P. aeruginosa exotoxin A (ETA).

The Vi-rEPA$_{II}$ conjugates of this invention induce a strong initial IgG antibody response in humans. In this respect, they have a significant advantage over the Vi-rEPA$_I$ conjugates.

DETAILED DESCRIPTION OF THE INVENTION

The invention provides methods of using conjugates of an S. typhi Vi polysaccharide which is covalently bound to the carrier rEPA with a dicarboxylic acid dihydrazide linker, preferably an adipic acid dihydrazide linker, and compositions thereof. The present invention also encompasses methods of using mixtures such S. typhi-rEPA conjugates and/or compositions thereof as part of a composition containing other immunogens, to form a multivalent vaccine for broad coverage against various pathogens. The S. typhi-rEPA conjugates, and/or compositions thereof, may also be administered concurrently with other vaccines, such as the DTP vaccine.

The invention also provides methods of using such S. typhi-rEPA conjugates, and/or compositions thereof, to induce in mammals, in particular, humans, the production of antibodies which immunoreact with the Vi polysaccharide of S. typhi. In the preferred embodiment, antibodies which immunoreact with ETA of P. aeruginosa are also produced. The antibodies which immunoreact with Vi of S. typhi may be useful for the identification, detection, and/or diagnosis of S. typhi colonization and/or infection. Antibodies against S. typhi may be useful to prevent and/or treat illnesses caused by S. typhi. Antibodies which immunoreact with ETA may be useful to prevent or treat illnesses caused by P. aeruginosa.

Pharmaceutical compositions of this invention are capable, upon injection into a human, of inducing serum antibodies against S. typhi. In general, the exemplified Vi-rEPA conjugate vaccine of this invention using ADH as the linker (i.e., Vi-rEPA$_{II}$) is capable of inducing serum IgG antibody levels which are statistically significantly higher than those induced by Vi alone or by Vi conjugated to rEPA using SPDP as the linker (i.e., Vi-rEPA$_I$). The induction by the immunogen, in ≧80% of the immunized population, of a ≧8-fold increase in anti-Vi IgG at four to six weeks after a proscribed course of vaccination with the immunogen has been completed, is usually required for an effective vaccine against typhoid fever.

Preferably, the method of the invention is capable, upon injection into an adult human of an amount of Vi-rEPA$_{II}$ vaccine containing 25 µg of S. typhi Vi polysaccharide, of inducing in the serum of the human a level of anti-Vi IgG antibody which, when measured six weeks after the injection, is at least about 48-fold higher than the anti-Vi IgG levels prior to injection.

Also preferably, the method of the invention is capable, upon injection into a five- to fourteen-year-old human of an amount of Vi-rEPA$_{II}$ vaccine composition containing 25 µg of S. typhi Vi polysaccharide, of inducing in the serum of the human a level of anti-Vi IgG antibody which, when measured six weeks after the injection, is at least about 252-fold higher than the anti-Vi IgG levels prior to injection.

Also preferably, the method of the invention is capable, upon injection into a two- to four-year-old human of an amount of Vi-rEPA$_{II}$ vaccine composition containing 25 µg of S. typhi Vi polysaccharide, of inducing in the serum of the human a level of anti-Vi IgG antibody which, when measured six weeks after the injection, is at least about 400-fold higher than the anti-Vi IgG levels prior to injection.

The Vi-rEPA vaccines of this invention are intended for active immunization for prevention of S. typhi infection, and for preparation of immune antibodies. The vaccines of this invention are designed to confer specific immunity against infection with S. typhi, and to induce antibodies specific to S. typhi Vi and ETA. The S. typhi conjugate vaccine is composed of non-toxic bacterial components, suitable for infants, children of all ages, and adults.

The methods of using the Vi-rEPA conjugates of this invention, and/or compositions thereof will be useful in increasing resistance to, preventing, ameliorating, and/or treating S. typhi infection in humans.

This invention also provides compositions, including but not limited to, mammalian serum, plasma, and immunoglobulin fractions, which contain antibodies which are immunoreactive with S. typhi Vi, and which preferably also contain antibodies which are immunoreactive with ETA. These antibodies and antibody compositions may be useful to prevent, treat, or ameliorate infection and disease caused by the microorganism. The invention also provides such antibodies in isolated form.

High titer anti-Vi sera, or antibodies isolated therefrom, may be used for therapeutic treatment for patients with S. typhi infection. Antibodies elicited by the Vi-rEPA conjugates of this invention may be used for the treatment of established S. typhi infections, and may also be useful in providing passive protection to an individual exposed to S. typhi.

The present invention also provides diagnostic tests and/or kits for S. typhi infection and/or colonization, using the conjugates and/or antibodies of the present invention, or compositions thereof.

The invention is intended to be included in the routine immunization schedule of infants and children, and in individuals at risk for S. typhi infection. It is also planned to be used for intervention in epidemics caused by S. typhi. Additionally, it is may be used as a component of a multivalent vaccine for S. typhi and other pathogens, useful for example for the routine immunization of infants.

Definitions

Vi is a linear homopolymer of α(1→4)-D-GalpA, which is N-acetylated at C-2 and O-acetylated at C-3.

As used herein, the terms "immunoreact" and "immunoreactivity" refer to specific binding between an antigen or antigenic determinant-containing molecule and a molecule having an antibody combining site, such as a whole antibody molecule or a portion thereof.

As used herein, the term "antibody" refers to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab') and F(v), as well as chimeric antibody molecules.

Polymeric Carriers

Carriers are chosen to increase the immunogenicity of the polysaccharide and/or to raise antibodies against the carrier which are medically beneficial. Carriers that fulfill these criteria are well known in the art. A polymeric carrier can be a natural or a synthetic material containing one or more functional groups, for example primary and/or secondary amino groups, azido groups, or carboxyl groups. Carrier can be water soluble or insoluble. The present invention concerns methods of using Vi conjugates with rEPA as a carrier.

Methods for Attaching Vi to rEPA

Methods for binding a polysaccharide to a protein, with or without a linking molecule, are well known in the art. See for example reference [8b], where 3 different methods for conjugating Shigella O-SP to tetanus toxoid are exemplified. See also, reference [31], which describes methods for conjugating S. typhi Vi and adipic hydrazide-derivatized protein.

In the present invention, attachment of the S. typhi Vi polysaccharide to a protein carrier is preferably accomplished by first coupling a dicarboxylic acid dihydrazide linker to rEPA, by treatment with a peptide coupling agent, preferably a water-soluble carbodiimide such as 1-ethyl-3-(3-dimethylaminopropyl)carbodiimide, 1-ethyl-3-(3-dimethylaminopropyl)-carbodiimide methiodide, or the like, to produce a hydrazide-functionalized carrier protein. Adipic acid dihydrazide is a preferred linker, but conjugates employing other linkers, such as the dihydrazides of succinic, suberic, and sebacic acids, are contemplated to be within the scope of the invention. The *S. typhi* polysaccharide, Vi, is then coupled to the hydrazide-functionalized carrier protein, again preferably with a water-soluble carbodiimide.

Regardless of the precise method used to prepare the conjugate, after the coupling reactions have been carried out the unbound materials are removed by routine physicochemical methods, such as for example gel filtration or ion exchange column chromatography, depending on the materials to be separated. The final conjugate consists of the polysaccharide and the carrier bound through a dihydrazide linker.

Dosage for Vaccination

The present inoculum contains an effective, immunogenic amount of a Vi-rEPA polysaccharide-carrier conjugate. The effective amount of polysaccharide-carrier conjugate per unit dose sufficient to induce an immune response to *S. typhi* depends, among other things, on the species of mammal inoculated, the body weight of the mammal, and the chosen inoculation regimen, as is well known in the art. Inocula typically contain polysaccharide-carrier conjugates with concentrations of polysaccharide from about 1 micrograms to about 500 micrograms per inoculation (dose), preferably about 3 micrograms to about 50 micrograms per dose, and most preferably about 5 micrograms to 25 micrograms per dose.

The term "unit dose" as it pertains to the inocula refers to physically discrete units suitable as unitary dosages for mammals, each unit containing a predetermined quantity of active material (polysaccharide) calculated to produce the desired immunogenic effect in association with the required diluent.

Inocula are typically prepared in physiologically and/or pharmaceutically tolerable (acceptable) carriers, and are preferably prepared as solutions in physiologically and/or pharmaceutically acceptable diluents such as water, saline, phosphate-buffered saline, or the like, to form an aqueous pharmaceutical composition. Adjuvants, such as aluminum hydroxide, may also be included in the compositions.

The route of inoculation may be intramuscular, subcutaneous or the like, which results in eliciting antibodies protective against *S. typhi*. In order to increase the antibody level, a second or booster dose may be administered approximately 4 to 6 weeks after the initial injection. Subsequent doses may be administered as indicated herein, or as desired by the practitioner.

Antibodies

An antibody of the present invention in one embodiment is characterized as comprising antibody molecules that immunoreact with *S. typhi* Vi.

An antibody of the present invention is typically produced by immunizing a mammal with an immunogen or vaccine containing an *S. typhi* Vi-rEPA polysaccharide-protein carrier conjugate to induce, in the mammal, antibody molecules having immunospecificity for the immunizing polysaccharide. Antibody molecules having immunospecificity for the protein carrier will also be produced. The antibody molecules may be collected from the mammal and, optionally, isolated and purified by methods known in the art.

Human or humanized monoclonal antibodies are preferred, including those made by phage display technology, by hybridomas, or by mice with human immune systems. The antibody molecules of the present invention may be polyclonal or monoclonal. Monoclonal antibodies may be produced by methods known in the art. Portions of immunoglobulin molecules, such as Fabs, may also be produced by methods known in the art.

The antibody of the present invention may be contained in blood plasma, serum, hybridoma supernatants and the like. Alternatively, the antibodies of the present invention are isolated to the extent desired by well known techniques such as, for example, ion chromatography or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection. The antibodies of the present invention have a number of diagnostic and therapeutic uses. The antibodies can be used as an in vitro diagnostic agents to test for the presence of *S. typhi* in biological samples or in meat and meat products, in standard immunoassay protocols. Such assays include, but are not limited to, agglutination assays, radioimmunoassays, enzyme linked immunosorbent assays, fluorescence assays, Western blots and the like. In one such assay, for example, the biological sample is contacted with first antibodies of the present invention, and a labeled second antibody is used to detect the presence of *S. typhi* to which the first antibodies have bound.

Such assays may be, for example, of direct format (where the labeled first antibody is reactive with the antigen), an indirect format (where a labeled second antibody is reactive with the first antibody), a competitive format (such as the addition of a labeled antigen), or a sandwich format (where both labeled and unlabelled antibody are utilized), as well as other formats described in the art.

The antibodies of the present invention are also useful in prevention and treatment of infections and diseases caused by *S. typhi*.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 1 mg/kg to about 10 mg/kg body weight of the mammal, although a lower or higher dose may be administered. The antibodies of the present invention are intended to be provided to the recipient subject in an amount sufficient to prevent, or lessen or attenuate the severity, extent or duration of the infection by S. typhi. Antibodies which immunoreact with ETA are intended to be provided to the recipient subject in an amount sufficient to prevent, lessen or attenuate the severity, extent or duration of an infection by ETA producing organisms, such as P. aeruginosa.

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided prior to the anticipated exposure to S. typhi (or other Shiga toxin producing bacteria), so as to attenuate the anticipated severity, duration or extent of an infection and disease symptoms, after exposure or suspected exposure to these bacteria, or after the actual initiation of an infection.

For all therapeutic, prophylactic and diagnostic uses, the polysaccharide-carrier conjugates of this invention, as well as antibodies and other necessary reagents and appropriate devices and accessories may be provided in kit form so as to be readily available and easily used.

The following examples are exemplary of the present processes and incorporate suitable process parameters for use herein. These parameters may be varied, however, and the following should not be deemed limiting.

EXAMPLE 1

Materials and Methods

Clinical protocol. The study was approved by the Ministry of Health of Vietnam, the Institutional Review Board of the National Institute of Child Health and Development, NMH and FDA. Informed consent was obtained from adults or from parents or guardians of vaccinees under 18 years old. The site was Cao Lanh District, Dong Thap Province in the Mekong Delta region of Vietnam. The vaccines were stored at 4° C. and injected intramuscularly into the deltoid muscle in 0.5 mL aliquots, containing 25 μg of Vi alone or as a conjugate. Twenty two teachers or administrative personnel of the Bon Sang Nursery, My-Tho Town, Cao Lanh District, received an injection of Vi-rEPA$_{II}$ (BB IND 6990). 157 5 to 14 year-olds, recruited from the elementary, middle and high school of Cao Lanh District, received 1 injection of 0.5 mL of either Vi-rEPA$_I$ (BB IND 4334), Vi-rEPA$_{II}$ or Vi (Lot K1140, manufactured by Pasteur-Merieux Serums et Vaccins and distributed by Connaught Laboratories, U.S. License 384).

A group of 203 2 to 4 year-olds, recruited from the Bon Sang Nursery, were randomized to receive either 1 or 2 injections of Vi-rEPA$_I$ or of Vi-rEPA$_{II}$ spaced 6 weeks apart. The groups are uneven because some individuals refused the second injection.

The teachers and the parents were instructed to examine the children at 6, 24 and 48 hours following the injection. Children who were absent on the ensuing 2 days were visited at home by the District Health medical staff. None of the recipients had erythema >1 cm at the injection site and none of the recipients had fever for 2 days following the injection.

Blood samples were taken before, and at 6 and 26 weeks after injection of the adults and 5–14 year-olds. An additional blood sample was taken from the 24 year-olds 10 weeks after the first injection.

Reagents: Dialysis tubing: Spectra/por, 45 mm, mwco=3500, 32 mm, mwco=8000, from Spectrum, Houston, Tex.; Biodesign #D102, 15.5, mwco=8000, Carmel, N.Y.; YM10 membrane, 62 mm, mwco=10,000 from Amicon, Beverly, Mass.; Filters: 150 mL unit, C.A., 0.45 μm, from Nalgene, Rochester, N.Y., 25 mm, 0.45 μm, Uniflow, from Schleicher & Schuell, Keen, N.H.; Chemicals: 2[-N-morpholino]-ethanesulfonic acid [MES], acid form, sodium form, [MES buffer (pH5.6), titrated with MES-Na and MES-H]; hydroxylamine, resorcinol, adipic acid dihydrazide [ADH], 1-ethyl-3-(3-dimethylaminopropyl) carbodiimide [EDC], thimerosal, from Sigma Chemical Co, St. Louis, Mo.; Tris, GIBCO, NY; Sephacryl S-1000, Sephadex G-50, from Pharmacia, Piscataway, N.J.; ammonium sulfate, Mallinckcrodt, Paris, Ky.; Limulus amebocyte lysate (LAL), lot 12-56-648, from Associates of Cape Cod Ind. Woods Hole, Mass.; U.S. standard endotoxin (RSE), lot EC-5, from Bureau of Biologics (CBER), FDA, Bethesda, Md.; Goat anti-exotoxin, lot GAE-02A from List Biological Lab., Inc., Campbell, Calif.; 2,4,6-trinitrobenzene sulfuric acid, Pierce Chemicals, Rockford, Ill.; Coomassie blue reagent, standard bovine serum albumin (BSA) solution (2 mg/mL), from Pierce Chemicals, Il.

Assays. EDC, protein, hydrazide were measured as described [31]. Vi content of conjugates was measured by determination of the O acetyl with Vi as a standard. Sterility, pyrogenicity, and general safety was assayed according to the Code of Federal Regulations (CFR) 610.126.

Vi (Lot 112A). Vi (3.2 μmol O-acetyl/mg, 1.2% nucleic acid, <0.01% protein) was obtained from Pasteur-Merieux, Serums et Vaccins, Lyon, France. This Vi (985 mg) was extracted with cold phenol 10 times. The water phase was dialyzed 4 times against 6 L of pyrogen-free water (PFW), 4° C. and freeze-dried. The final yield of Vi was 50%. The endotoxin content, determined by Limulus Amebocyte Lysate (LAL), was 25–50 EU/μg.

rEPA. Recombinant exoprotein A (rEPA) is a genetically manipulated non-toxic, fully antigenic derivative of Pseudomonas aeruginosa exotoxin A (ETA) secreted by the recombinant strain of Escherichia coli BL21(IDE3) carrying plasmid pVC45D. Fermentation of E. coli BL21(IDE3) and purification of rEPA was performed as described [10]. Fractions containing rEPA were pooled, dialyzed against pyrogen-free saline (PFS), 50 mM sodium phosphate (PBS), pH 7.2, sterile filtered and ultracentrifuged at 100,000×g for 5 hours at 4° C. The pellet was discarded and the supernatant (25 mL) was sterile-filtered. The endotoxin content of rEPA was <1 EU/mg. rEPA showed no toxicity in mice at 500 times the lethal dose of ETA.

VirEPA$_I$ (SPDP). Vi-rEPA$_I$ (lot 61411) was prepared using N-succinimidyl-3-(2-pyridyl dithio) propionate (SPDP) as a linker [51, 54]. Cystamine (360 mg), dissolved in 20 mL of PFS, was mixed with 120 mg of Vi (lot 112A) and the pH brought to 5.0 with 0.1M NaOH in an autotitrator. EDC was added to a final concentration of 0.1M and the pH maintained at 5.0 for 3 hours by addition of 0.1M HCl. The reaction mixture was dialyzed against PFW at 5° C. and freeze-dried. The SH concentration was 1.3% w/w.

SPDP, 14 mg/1.6 mL ethanol, was added to 7 mL of rEPA (10 mg/mL) with stirring for 2 hours at room temperature and overnight at 4° C. The reaction mixture was passed through a Bio-Gel P-6DG in PBS, 1 mM EDTA, pH 7.2, the void volume concentrated, sterile-filtered, and stored at 4° C. The SPDP/rEPA was 10.6 mol/mol. A single line of precipitation was formed between rEPA and the rEPA-SPDP derivative (not shown).

Dithiothreitol (DTT) (37.2 mg) was added to 3 mL of Vi-cystamine (10 mg/mL in PFS, 10 mM sodium phosphate, pH 7.2 (PBS)) for 2 hours at room temperature. The reaction mixture was passed through Bio-Gel P6DG in PFS. Void volume fractions were sterile-filtered and added to 4.0 mL of rEPA-SPDP (31.5 mg). The reaction mixture was stirred at room temperature for 2 hours and passed through a column of S-1000 Sephacryl in PBS, pH 7.2 at 4° C. Fractions were monitored for protein, O-acetyl, and by immunodiffusion. A pool of conjugate-containing fractions (71 µg/mL protein and 75 µg/mL Vi) was denoted as Vi-rEPA$_I$ Rabbit anti-ETA and burro anti-Vi reacted with an identical precipitation line with Vi-rEPA$_I$ and did not enter 10% PAGE in 1% SDS (not shown).

Vi-rEPA$_{II}$ (ADH). 0.5M MES buffer, pH 5.6 (4.6 mL), was added to 24.6 mL of rEPA (300 mg): the resultant pH was 5.7. With stirring, ADH (1.05 g) was added followed by EDC (60.8 mg) and maintained for 1 hour at room temperature. The pH was stable at 5.6. The reaction mixture was dialyzed against PBS at 4° C., centrifuged at 14,500×g for 30 minutes at 4° C., and the supernatant passed through a 5×87 cm column of Sephadex G-50 in 0.2 M NaCl, 0.25 mM phosphate, pH 7.0. The void volume fractions were concentrated over a YM-10 membrane at $N_2$ pressure of 150 kPa and sterile-filtered. The ratio of hydrazide/protein of rEPA-AH was 0.023 (w/w) or 8.7 (mol/mol). SDS-PAGE (8% acrylamide) showed a similar pattern of rEPA-AH compared to rEPA (not shown). rEPA-AH and rEPA formed a line of identity with goat anti-ETA (not shown).

Vi, 100 mg of Vi (10 mg/mL PFS) was mixed with 2.4 mL of 0.5 M MES buffer pH 5.6 at room temperature. With mixing, 63 mg of EDC was added and after 2 minutes, 100 mg of rEPA-AH (10.1 mg/mL) was added dropwise. The reaction mixture was brought to 33.3 mL with 11 mL of PFS so that the concentration of Vi and rEPA was 3 mg/mL and 10 mM for EDC. The pH rose gradually from 5.5 to 5.7 within 3 hours of reaction, then the pH was brought up to 7.0 with several drops of 1M sodium phosphate buffer, pH 7.0. The mixture was stored at 4° C. overnight, centrifuged for 30 minutes at 14,500×g, 10° C. and passed through a 2.5×90 cm Sephacryl S-1000 column in phosphate buffered saline, pH 7.0, (PBS, pyrogen-free saline containing 5mM sodium phosphate pH 7.0, and 0.01% thimerosal). Fractions #23 through 50 were pooled and the bulk of Vi-rEPA contained 200.3 µg Vi/ml and 171.1 µg rEPA/ml. The bulk was 4-times diluted with the PBS and the resultant Vi-rEPA$_{II}$ was bottled. The bottled conjugate vaccine contained 48 µg Vi/ml and 43 µg rEPA/ml.

Immunogenicity in mice and in guinea pigs: Vi or the Vi conjugates were diluted to 25 µg/mL in saline and 0.1 mL injected subcutaneously three times 2 weeks apart in 6 week-old female general purpose mice (10 mice/group). Controls were injected once with saline or three times with Vi alone. Mice were exsanguinated 7 days after each injection and assayed for total Vi antibody by ELISA using a pooled murine hyperimmune serum, containing 500 µg anti-Vi/mL, as a reference.

Three vaccines, containing 5 µg of saccharide, were injected into groups of 4 6-week-old Duncan-Hartley guinea pigs and serum anti-Vi assayed by ELISA as described (performed by Pasteur Mérieux).

Double immunodiffusion. Vi, rEPA, rEPA-AH, and the two conjugates were reacted with burro anti-Vi (B260) and goat anti-EPA and sera from mice after their second injection of conjugates were assayed by double immunodiffusion against 100 µg Vi/mL as described [31].

ELISA. Total anti-Vi was assayed in murine and in guinea pig sera as described [31]. IgG was extracted from 500 mL of plasma from an adult vaccinated with Vi polysaccharide typhoid vaccine. The anti-Vi content of this human IgG was assayed by RIA by Pasteur Merieux Serum et Vaccins, Lyon, France. Sera were assayed for IgG, IgM and IgA anti-Vi by ELISA [31]. Goat anti-human IgG (Jackson Immuno Research Laboratories, Inc) and IgM (Sigma Chemical Company) conjugated to alkaline phosphatase were used as secondary antibodies. Serum from a typhoid carrier with high titer of IgM anti-Vi IgM was assigned a value 100 EU and used as a reference for this Ig. The levels of anti-Vi were calculated as a percent of the standard and expressed as the geometric mean and the 25–75 centiles for IgG and for IgM anti-Vi. Confirming previous results, the correlation coefficient was r=0.964 between the level of IgG anti-Vi assayed by RIA and ELISA and 0.084 for IgM. Antibody levels are expressed as the geometric mean and the 25th and 75th centiles.

Data analysis. Comparisons of geometric means were performed by paired and unpaired t tests when appropriate.

EXAMPLE 2

Composition of the Vaccines

Because the immunogenicity is related to $M_r$ of Vi, we used the highest molecular weight Vi available for our conjugates. Vi passes through Sephacryl S-1000 and the CL-2B Sepharose starting from the void volume. SDS-PAGE of the fractions showed a Coomassie Blue-staining band that did not move through the gel: there were no bands in the gel. Double immunodiffusion showed a stained circle around the edge of the antigen wells and two precipitation lines that did not cross, one positive with anti-Vi and the other with anti-ETA sera. Accordingly, we cannot yet distinguish bound (conjugated) from unbound Vi. The specifics for the sterility and general safety tests in Code of Federal Regulations 610.11 should be met.

Vi-rEPA$_{II}$ did not give a positive reaction with the sensitivity of the assay at $2.6 \times 10^{-5}$ M carbodiimide. 10% SDS PAGE of Vi-rEPA$_I$ or of Vi-rEPA$_{II}$ showed one band at the top of the gel (did not enter the gel). No bands corresponding to the rEPA-AH or rEPA were detected. In HPLC profiles of Vi(lot 126A), Vi-rEPA$_I$ and of Vi-rEPA$_{II}$, and rEPA on TSK-G6000, Vi eluted as a single broad peak at 19.96 minutes and rEPA-AH eluted at 24.27 minutes. Both Vi-rEPA$_I$ and Vi-rEPA$_{II}$ showed one peak at 16.67 minutes with $A_{280}$.

TABLE 1

Vi polysaccharides from Pasteur Mérieux, Serum et Vaccins, Lyon, France.

|  | Lot 65332 (Vi-rEPA$_{II}$) | Lot 51706 (Vi-rEPA$_1$) |
| --- | --- | --- |
| Pasteur Mérieux | Vi112A | Vi104A |
| O-acetyl | 3.19 µmoles/mg | 2.97 µmoles/mg |
| $M_r$ | 60.3% < Kd 0.25 | 60.5% < Kd 0.25 |
| Nucleic acid | 1.2% | 1.4% |

TABLE 1-continued

Vi polysaccharides from Pasteur Mérieux, Serum et Vaccins, Lyon, France.

|  | Lot 65332 (Vi-rEPA$_{11}$) | Lot 51706 (Vi-rEPA$_1$) |
|---|---|---|
| Protein | <0.1% | <0.1% |
| Pyrogen | Passes 0.01 μg/kg | Passes 0.01 μg/kg |

Both lots of Vi pass the requirements of the World Health Organization for Vi typhoid polysaccharide vaccine.

EXAMPLE 3

Immunogenicity in Mice

After one injection, mice immunized with either conjugate had higher levels of anti-Vi than Vi alone (13,4, 112.5 vs 5.78 p=0.01). In contrast to Vi, both conjugates elicited a booster response after the second injection (79.5 vs 12.5, 109 vs 13.4, p=0.01): Vi-rEPA$_{II}$ elicited higher levels of anti-Vi than Vi-rEPA$_I$ (109 vs 79.5, p=0.05). See Table 2. Sera from the mice after the second injection of either conjugate precipitated with Vi in double immunodiffusion (not shown).

TABLE 2

Geometric mean serum anti-Vi (μg/mL) elicited in mice by subcantaneous injection of Vi, Vi-rEPA$_1$ and Vi-rEPA$_{11}$

| Immunogen | n = | 1st injection | 2nd injection |
|---|---|---|---|
| Saline | 5 | 0.05 | Not done |
| Vi, Lot 104A | 10 | 1.37 | Not done |
| Vi, Lot 112A | 10 | 3.72 | Not done |
| Vi-rEPA$_1$ | 10 | 8.82 | 59.2 |
| Vi-rEPA$_{11}$* | 10 | 12.6 | 79.5 |
| 12.6 vs 8.82, p = NS; 79.5 vs 59.2, p = NS | | | |

*Reported in Reference 31 as Vi-rEPA$_8$. Mice were injected with 2.5 μg Vi alone or as a conjugate as described in MATERIALS AND METHODS.

Numbers for Vi Lot 104A and for related conjugate Vi-rEPA$_I$ are reported in Ref. 54 (see general purpose mice experiment). Results are in μg anti-Vi/mL (measured by RIA).

Vi-rEPA$_{II}$ and related Lot of Vi 112A (used for making this conjugate) were made and tested in animals years after Vi-rEPA$_I$ was made and tested in mice, guinea pigs and adults. Immunogenicity of Vi-rEPA$_I$, was tested by ELISA, not RIA, but because results are expressed in μg anti-Vi-mL using the same standard serum, the numbers in Table 2 are comparable.

EXAMPLE 4

Immunogenicity in Guinea Pigs

As reported, Vi did not elicit anti-Vi in guinea pigs after two injections [31]. Neither conjugate induced anti-V$_I$ after the first injection and both conjugates elicited anti-Vi after the second injection, but only Vi-rEPA$_{II}$ elicited a statistically significant rise of the GM anti-Vi level after the third injection. See Table 3.

TABLE 3

Geometric mean serum IgG anti-Vi (ELISA units) elicited in guinea pigs (n = 4) by injection of Vi, Vi-rEPA$_1$ and Vi-rEPA$_{11}$

| Immunogen | 1st injection | 2nd injection | 3rd injection |
|---|---|---|---|
| Saline | <10 | <10 | Not done |
| Vi, Lot 104A | <2 | <2 | <2 |
| Vi, Lot 112A | <10 | <10 | <10 |
| Vi-rEPA$_1$ | <31 | 384 | 167 |
| Vi-rEPA$_{11}$* | <10 | 60 | 54 |

*Reported in Reference 31 as Vi-rEPA$_8$. Mice were immunized with Vi vaccines as described in MATERIALS AND METHODS. Geometric mean serum anti-Vi is expressed as percent of a reference serum.

Vi-rEPA$_I$ is reported in Ref. 54. Results from the guinea pig experiment with Vi-rEPA$_I$ and Vi Lot 104 cannot be compared with Vi-rEPA$_{II}$, because they are expressed in arbitrary ELISA units referring to different standard sera.

EXAMPLE 5

Clinical Reactions

None of the volunteers had fever following either the first or second injection. Local reactions were confined to mild pain in a small fraction of the vaccinees at any age.

Anti-VI in adults (Table 4). In the present study, only Vi-rEPA$_{II}$ was evaluated in adults. All volunteers had significantly higher preexisting anti-Vi than those of the 5–14 year-olds (9.62 vs 0.44, 0.42, 0.61, p=0.0001). Six weeks after injection, all vaccinees responded with >4 rise in anti-Vi of the 3 Ig classes: 48-fold rise of IgG (465 vs 9.62, p=0.0001), 5-fold rise of IgM (19.0 vs 4.76, p=0.0001) and a 43-fold rise of IgA (8.85 vs 0.20, p=0.0001). The IgG anti-Vi fell to 119 (3.9-fold decline) at 26 weeks, but this level was 12.4-fold higher than the pre-vaccination levels (119 vs 9.62, p=0.0O00). Similarly, at the 26 weeks interval, IgM and IgA anti-Vi declined but were significantly higher than the pre-immune values (p<0.01).

TABLE 4

Serum anti-Vi (μg/mL) in adults (n = 22) elicited by one injection of Vi-rEPA$_{11}$

|  |  | Pre-injection | 6 weeks | 26 weeks |
|---|---|---|---|---|
| IgG: | Geometric mean | 9.62 | 465 | 119 |
|  | 25–75 centiles | 5.0–20.8 | 293–894 | 52.8–277 |
|  | 465, 119 vs 9.62, p = 0.0001; 465 vs 119, p = 0.0001 | | | |
| IgM: | Geometric mean | 4.76 | 19.0 | 9.34 |
|  | 25–75 centiles | 2.68–7.48 | 6.27–36.2 | 4.78–18.2 |
|  | 19.0, 9.34 vs 4.76, p < 0.001; 19.0 vs 9.34, NS | | | |
| IgA: | Geometric mean | 0.20 | 8.85 | 4.99 |
|  | 25–75 centiles | 0.10–0.30 | 1.92–18.2 | 1.22–10.7 |
|  | 8.85, 4.99 vs 0.20, p = 0.0001; 8.85 vs 4.99, p < 0.0001 | | | |

NS = Not statistically significant

Vi-rEPA$_I$ was evaluated in adults in a previous study using 15 ug polysaccharide per injection, as reported in reference 54.

Anti-Vi In 5–14 year-olds (Table 5). On a random basis, the 5–14 year-olds were injected once with Vi or 1 of the 2 conjugates. All 4 groups had similar levels of pre-injection anti-Vi that were significantly lower than those of adults (vide supra).

TABLE 5

Serum anti-Vi of 5 to 14 year-olds injected with Vi, Vi-rEPA$_1$ or Vi-rEPA$_{11}$

| | Geometric mean ELISA Units (25–75th centiles) | | |
|---|---|---|---|
| | Vi | Vi-rEPA$_1$ | Vi-rEPA$_{11}$ |
| IgG: Pre- | 0.44 (0.28–0.59) | 0.42 (0.24–0.53) | 0.67 (0.24–1.81) |
| 6 wks | 18.9 (7.84–44.1) | 22.8 (7.86–58.9) | 169.0 (80.8–290) |
| 26 wks | 13.4 (6.01–29.4) | 10.8 (3.64–28.8) | 30.0 (14.1–45.5) |
| | 30.0 vs 13.4, 10.8; p < 0.001 | | |
| IgM: Pre- | 6.47 (4.02–9.90) | 6.75 (4.16–10.2) | 5.79 (3.33–8.25) |
| 6 wks | 25.2 (17.4–40.3) | 48.0 (21.0–81.1) | 92.1 (51.5–154) |
| 26 wks | 12.3 (6.64–21.2) | 26.2 (13.0–49.0) | 31.3 (17.9–56.7) |
| | 31.3 vs 26.2 NS; 31.3 vs 12.3 p = 0.0001; 31.3, 26.2 vs 12.3 p = 0.0002 | | |
| IgA: Pre- | 0.05 (0.03–0.07) | 0.03 (0.02–0.04) | 0.05 (0.02–0.10) |
| 6 wks | 2.64 (0.81–7.59) | 1.99 (0.73–5.13) | 16.5 (9.19–43.5) |
| 26 wks | 2.04 (0.81–6.72) | 0.99 (0.35–2.77) | 4.99 (3.34–28.9) |
| | 4.99 vs 2.04, NS; 4.99 vs 0.99, p = 0.02 | | |

All three vaccines elicited significant rises of anti-Vi of the 3 isotypes at 6 and at 26 weeks over the pre-immune levels. Vi-rEPA$_{11}$ elicited higher levels of anti-Vi at all intervals than Vi-rEPA$_1$ and Vi.

IgG anti-Vi. At 6 weeks, all responded with >4-fold rises of anti-Vi: 43-fold for Vi, 54-fold for Vi-rEPA$_I$ and 252-fold for Vi-rEPA$_{II}$. Vi-rEPA$_{II}$ elicited higher levels of anti-Vi than Vi-rEPA$_I$ or Vi (169 vs 22.8, 18.9 p=0.000 1). Twenty six weeks later, the IgG anti-Vi of all groups declined but remained >4 fold higher than the pre-immune levels: Vi-rEPA$_{II}$>Vi>Vi-rEPA$_I$ (30.0 vs 13.4,10.8, p=0.0001). Of interest, is that similar levels of IgG anti-Vi were elicited by Vi-rEPA$_I$ and Vi at both 6 and 26 weeks following vaccination.

IgM anti-Vi. Pre-immune levels of the three groups were similar. At the six weeks interval, all the vaccines elicited significant rises of anti-Vi (25.2 vs 6.47, 48.0 vs 6.75, 92.1 vs 5.79; p=0.0001, for Vi, Vi-rEPA$_I$, for Vi-rEPA$_{II}$, respectively). Vi-rEPA$_I$ induced higher anti-Vi than Vi alone at both post vaccination intervals (p<0.0002). At 26 weeks, the GM IgM anti-Vi of the three groups were higher than the pre-immune levels: the levels in the recipients of the conjugates were higher than that of Vi (31.3,26.2 vs 12.2; p<0.01).

IgA anti-Vi. The pre-immune levels of the three groups were similar and almost at the level of detection. Vi-rEPA$_{II}$ elicited the highest IgA anti-Vi of the 3 vaccines (16.5 vs 1.99, 2.64; p<0.002). The levels of the 3 groups declined at 26 weeks but this order of IgA anti-Vi was retained at 26 weeks (4.99 for Vi-rEPA$_{II}$ vs Vi-rEPA$_I$, 2.04; NS; 4.99 vs 0.99, p=0.02). The 26 week level elicited by Vi-rEPA$_{II}$ (4.99) was higher than the 6 week level in the groups receiving Vi (2.04) and Vi-rEPA$_I$ (1.99).

One vs 2 injections of Vi conjugates in 2 to 4 year-olds (Table 6) Vi was not administered to the 2–4 year-olds. On a random basis, 2–4 year-olds were administered 1 or 2 injections of Vi-rEPA$_I$ or Vi-rEPA$_{II}$ 6 weeks apart: blood was taken before each injection and 4 and 26 weeks after the second injection. The pre-immune levels of the 4 groups were similar and slightly lower than those of the 5–14 year-olds. Six weeks after the first injection, all responded with >4 fold rise of anti-Vi of each Ig class and there was no significant difference for each conjugate between the groups destined to receive 1 or 2 injections.

TABLE 6

Serum anti-Vi of 2–4 year-olds injected 1 or 2 times 6 weeks apart with Vi-rEPA$_1$ or Vi-rEPA$_{11}$ (~50/group)

| | Geometric mean µg Ab/mL (25–75th centiles) | | | | | | | |
|---|---|---|---|---|---|---|---|---|
| | Vi-rEPA$_1$ | | | | Vi-rEPA$_{11}$ | | | |
| | 1 inj. | | 2 inj. | | 1 inj. | | 2 inj. | |
| IgG Pre | 0.32 | (0.23–0.40) | 0.33 | (0.23–0.43) | 0.19 | (0.10–0.27) | 0.18 | (0.11–0.23) |
| 6 wk | 30.2 | (15.2–53.5) | 28.9 | (18.0–53.0) | 77.2 | (41.3–165) | 69.9 | (36.5–126) |
| 10 wk | 21.4 | (10.9–39.8) | 83.0 | (46.3–185) | 54.3 | (34.5–165) | 95.4 | (60.0–126) |
| 26 wk | 5.50 | (2.90–9.80) | 12.8 | (9.66–25.1) | 20.4 | (9.82–40.9) | 30.6 | (22.4–51.6) |
| | 77.2, 69.9 vs 30.2, 28.9, p = 0.0001; | | | | | | | |
| | 95.4, 83.0 vs 18.9, 22.8 (Table 5), p = 0.0001; | | | | | | | |
| | 95.4 vs 83.0, NS; 30.6 vs 20.4, NS; 30.6 vs 12.8, 5.50, p = 0.0001 | | | | | | | |
| IgM: Pre- | 4.72 | (2.67–7.90) | 5.00 | (3.06–7.48) | 3.61 | (2.50–4.80) | 3.93 | (2.84–5.18) |
| 6 wk | 37.7 | (24.1–55.2) | 41.8 | (26.0–42.7) | 47.5 | (27.8–81.5) | 39.8 | (22.9–57.5) |
| 10 wk | 35.7 | (20.3–65.2) | 82.5 | (51.2–155) | 34.8 | (20.1–58.6) | 31.8 | (19.3–48.6) |
| 26 wk | 19.5 | (12.2–29.4) | 36.2 | (21.8–62.1) | 20.1 | (13.1–32.3) | 19.5 | (12.8–30.6) |
| IgA: Pre- | 0.02 | (0.01–0.02) | 0.02 | (0.01–0.02) | 0.02 | (0.01–0.02) | 0.02 | (0.01–0.02) |
| 6 wk | 1.76 | (1.30–2.54) | 1.32 | (0.71–3.34) | 6.23 | (2.79–18.1) | 5.68 | (2.22–12.9) |
| 10 k | 1.48 | (1.03–2.68) | 2.00 | (0.74–3.69) | 4.21 | (1.86–9.90) | 4.99 | (2.24–11.8) |
| 26 wk | 0.70 | (0.50–1.12) | 0.85 | (0.50–2.02) | 3.00 | (1.37–8.49) | 2.62 | (1.09–7.29) |
| | 3.00, 2.62 vs 0.70, 0.85 p < 0.02; 6.23 vs 5.68, 4.21 vs 4.99, 3.00 vs 2.62, NS | | | | | | | |

On a random basis, 2–4 year-olds were injected 1 or 2 times 6 weeks apart with Vi-rEPA$_1$ or Vi-rEPA$_{11}$. Blood was drawn before each injection and 4 and 20 weeks after the 2nd injection. NS = not statistically significant.

IgG anti-Vi: Vi-rEPA$_{II}$ elicited higher levels of anti-Vi than Vi-rEPA$_I$ (77.2,69.9 vs 30.2, 28.9, p=0.0001). The levels of anti-Vi in the 2–4 year-olds receiving Vi-rEPA$_{II}$ were higher than those administered Vi alone in the 5–14 year-olds (77.2,69.9 vs 18.9; p=0.0001). Four weeks after the second injection, both conjugates elicited a rise in anti-Vi (2.87-fold for Vi-rEPA$_I$ and 1.36fold for Vi-rEPA$_{II}$: levels elicited by 2 injections of Vi-rEPA$_{II}$ were only slightly higher than those by Vi-rEPA$_I$ (95.4 vs 83.0, NS). The second injection of both conjugates elicited higher levels of anti-Vi than one injection of the Vi or Vi-rEPA$_I$ in the 5–14 year-olds (95.4, 83.0 vs 18.9, 22.8; p=0.0001). At 26 weeks, IgG anti-Vi of the recipients of 2 injections of Vi-rEPA$_{II}$ were the highest (30.6 vs 20.4, 12.8, 5.50), similar to that of the 5–14 year-olds receiving the same conjugate but higher than the recipients of Vi alone in that age group (30.6 vs 13.4, p=0.0001). Serum IgG anti-Vi in the recipients of 2 injections of Vi-rEPA$_{11}$ at 26 weeks were slightly different for the 3 (20.7, n=19) and 4 year-olds (31.4, n=12) compared to the 2 year-olds (20.7, n=6) but these differences were not statistically significant.

IgM anti-Vi. IgM anti-Vi levels in all groups were similar and slightly lower than the 5–14 year-olds. One injection of either conjugate elicited about an 8-fold increase: there were no significant differences between the two conjugates. Unexpectedly, reinjection of Vi-rEPA$_I$ (82.5 vs 41.8; p=0.0003), but not Vi-rEPA$_{II}$ (31.8 vs 39.8; NS), elicited a booster response. At 26 weeks, the group that received Vi-rEPA$_I$ had the highest level; the levels were similar for the others (36.2 vs 19,5, 20.1, 19.5; NS)

IgA anti-Vi. Both conjugates elicited a significant rise of IgA anti-Vi: Vi-rEPA$_{II}$ higher than Vi-rEPA$_I$ (6.23, 5.68 vs 1.87, 1.36; p=0.02). Reinjection of Vi-rEPA$_I$ only elicited a slight rise of IgA anti-Vi (2.00 vs 1.32, NS). The levels of all groups declined at 26 weeks although all were significantly higher than those of the pre-immune sera: the recipients of 1 or 2 injections of Vi-rEPA$_{II}$ were similar and higher than those of the groups that received Vi-rEPA$_I$ (3.00, 2.62 vs 0.70, 0.85; p<0.02).

Anti-rEPA. Anti Vi-rEPA elicited higher levels of IgM anti-Vi than Vi alone in 5–14 year olds (data not shown).

Discussion of Initial Clinical Trials

As shown for other polysaccharides, such as *Haemophilus influenzae* type b, the immunogenicity of Vi is improved by covalently binding it to a protein. Previously, we reported the enhanced immunogenicity of conjugates compared to Vi, similar to Vi-rEPA$_I$, in adults [54].

Since reinjection of Vi and other polysaccharide-protein conjugates in older children or in adults does not elicit a booster response, only 1 injection of Vi conjugates and Vi were compared in 5 to 14 year-olds. Unexpectedly, at 6 and at 26 weeks after vaccination, IgG anti-Vi levels elicited by Vi-rEPA$_I$ and by Vi were similar at 6 (22.8 vs 18.9) and at 26 weeks (10.8 vs 13.4). Vi-rEPA$_I$, however, elicited higher levels of IgM anti-Vi than Vi at 6 (48.0 vs 25.2) and at 26 weeks (26.2 vs 12.3). Vi-rEPA$_{II}$ elicited higher levels of IgG, IgM and IgA anti-Vi at all intervals in the 5 to 14 year-olds than Vi-rEPA$_I$ and Vi.

In the 2–4 year-olds at 26 weeks, IgG anti-Vi levels elicited by Vi-rEPA$_{II}$ were higher than those elicited by Vi-rEPA$_I$ after 1 (20.4 vs 5.50, p=O.01) and 2 injections (30.6 vs 20.4), but these latter differences were not statistically significant. Two injections of Vi-rEPA$_{II}$ elicited higher levels than Vi in the 5–14 year-olds and, therefore, it can be predicted that this Vi conjugate will elicit greater than 70% efficacy when injected 2 times in individuals 22 years of age. In fact, in a clinical efficacy trial in 2–5 year-olds in Vietnam, where typhoid fever is endemic, this Vi conjugate (i.e., Vi-rEPA$_{II}$) demonstrated greater than 91% efficacy in preventing typhoid fever. (See Example 6, hereinbelow).

There is evidence that a critical (protective) level of serum IgG anti-Vi is sufficient to confer immunity to typhoid fever. In passive immunization experiments with serum taken mice and humans injected with cellular vaccines, IgG anti-Vi accounted for the protection against challenge with *S. typhi*. By analogy to *H. influenzae* type b and other capsulated pathogens it is antibodies of the IgG isotype, not IgM or IgA, that exude onto the epithelial surface and account for most of the serum anti-Vi in the intestine. We suggest that measurement of serum IgG anti-Vi will be essential and sufficient to standardize Vi conjugate vaccines.

We are yet unable to demonstrate by physico-chemical or immunologic methods whether there is some free Vi (unbound to protein) in our new conjugate. Vi is molecularly polydisperse material that cannot be 100% effectively separated from Vi conjugates on the available gel filtration media or polyacrylamide gels. Similarly, double immunodiffusion with antibodies to the Vi and to the carrier protein (rEPA) does not yield a precipitin line of identity. For the present, our only method for identifying that the Vi and protein are covalently bound is to demonstrate the increased immunogenicity of our conjugate in mice and in guinea pigs compared to mixtures of Vi and the adipic hydrazide-derivatized protein. [See, e.g., ref. 31].

Summary of Initial Clinical Trials

A Vi conjugate, prepared by treatment of an adipic hydrazide derivative of rEPA and Vi with EDC (Vi-rEPA$_{II}$), was shown to be safe and more immunogenic in mice, guinea pigs and in young children and adults than a similar construct made with SPDP. Vi-rEPA$_{II}$ elicited a booster response in 24 year-olds that results in levels of IgG anti-Vi significantly higher than those achieved by Vi alone in 5 to 14 year-olds. This new Vi conjugate is safe and can be expected to confer a high degree and long-lived immunity against typhoid fever in children as well as in adults.

One injection of Vi-rEPA$_{II}$ into adults (n=22) elicited 465 ELISA U/mL (48-fold geometric mean rise) of IgG anti-Vi at 6 weeks that fell to 119 after 26 weeks: similar patterns were observed for IgM and IgA anti-Vi. In 5–14 year-olds (~50/group), one injection of Vi elicited a 43-fold rise of IgG anti-Vi, Vi-rEPA$_I$ a 54-fold rise (54 vs 43, NS) and Vi-rEPA$_{II}$ a 252-fold rise (252 vs 54,43 p=0.0001). At 26 weeks, Vi-EPA$_{II}$ elicited 30.0 units of IgG anti-Vi that was higher than that induced by Vi-rEPA$_I$ and Vi (10.8 vs 13.4, NS); all were higher than pre-immune levels (p=0.0001). Vi-rEPA$_{II}$ elicited the highest IgM and IgA anti-Vi at 6 weeks and at 26 weeks.

One or two injections of Vi-rEPA$_I$ and Vi-rEPA$_{II}$ were evaluated in the 2–4 year-olds (~50 group). After 6 weeks there was a 406-fold rise of IgG anti-Vi in recipients of Vi-rEPA$_{II}$ and 94-fold rise in recipients of Vi-rEPA$_I$ (p=0.0001). Four weeks after a second injection, recipients of Vi-rEPA$_I$ and Vi-rEPA$_{II}$ had a rise of IgG anti-Vi: 83.0 from 28.9 and 95.4 from 69.9, respectively. At 26 weeks, the IgG anti-Vi levels of all vaccinees were higher than the pre-immune levels (p=0.0001). IgG anti-Vi levels elicited by 2 injections were higher than those with only 1 injection (30.6 vs 20.4 for Vi-rEPA$_{II}$ and 12.8 vs 5.50 for Vi-rEPA$_I$): IgG anti-Vi levels elicited by 2 injections of Vi-rEPA$_{II}$ were higher than those elicited by Vi in the 5–14 year-olds (30.6 vs 13.4, p=0.01). In all three age groups, Vi-rEPA$_{II}$ was more immunogenic than Vi-rEPA$_I$. Similar values were obtained for IgM and IgA anti-Vi. One injection of Vi-rEPA$_{II}$ should confer a higher degree of immunity to typhoid fever than Vi in individuals 25 years: 2 injections should confer comparable immunity in 2 to 4 year-olds to that in individuals 25 years of age.

EXAMPLE 6

Efficacy Trial

Methods

Study Design

The Study Protocol was approved by the Institutional Review Boards of the National Institute of Child Health and Human Development (NICHD) (Number OH-98-CH-N002) and that of the Ministry of Health, Vietnam, by the Center for Biologics Evaluation and Research, Food and Drug Administration (BB-IND 6990) and was assigned a Single Project Assurance (Number S-11089-07) by the Office for Human Research Protection, U.S. Department of Health and Human Services.

In November, 1997, a census of 16 communes in the Cao Lanh District, Dong Thap Province in the Mekong Delta of Vietnam, identified 14,285 2 to 5 year-olds. Almost all of the households relied upon river and rain as a source of water. Cao Lanh District is served by The Provincial Hospital and each commune (5,000 to 20,000 population) has a health center with a physician, assistant physicians, nurses, and approximately 20 community health workers. Approximately 95% of the population is engaged in agriculture.

Enrollment

Informed consent for 13,776 2 to 5-year-olds (96.4%) was obtained from the parents/guardians during group meetings and/or house visits conducted by the health workers. Excluded were children who required on-going medical care. Children with parental consent received a health card with an unique seven digit identification number.

Vaccines

Vi-rEPA was prepared and characterized as described.[27-29] The Vi-rEPA conjugate contained 22.5 μg Vi (Aventis Pasteur, Lot 126A, Lyon, France) and 22 μg of rEPA in 0.5 mL of saline, 0.01% thimerosal: its appearance from that of the placebo was indistinguishable. The 5-dose vials, containing 2.8 mL each of Vi-rEPA or of placebo, were labeled with a number from 0 through 9 on a random basis and packaged 10 per box. The code, kept by the Pharmacy Department, Clinical Center, NIH and by the Chairman, Safety Monitoring Committee, Ho Chi Minh City, Vietnam, was opened on Jun. 23, 2000.

Vaccination Protocol

Two rounds of vaccination were held in 1998. The first was from February 21 through March 9 and the second from April 4 through April 20. Vaccinations were conducted by 64 teams. Children were injected 2 times approximately 6 weeks apart with 0.5 mL from a vial with a number identical to the last digit of his/her identification number. Prior to injection, the children were examined by the health staff and their axillary temperatures taken. Those with no fever (<37.5° C.) were injected into the left deltoid and the vial number recorded. The children were observed for 20 minutes, their temperature taken and the injection site inspected for redness and swelling at 6, 24 and 48 hours by a community health worker.

Case Detection

The diagnosis of typhoid fever was made only on the demonstration of S. typhi from a blood culture. Recipients were visited weekly and their history and axillary temperature taken by community health workers. Children with fever ($\geq 37.5°$ C.) for at least 3 days were referred to the health station and 6 mL of blood drawn: 5 mL were delivered to Difco BACTO Blood Culture bottle, #0936-37-6 and 1 mL for serology. Blood cultures were maintained at 37° C. and the clotted blood at refrigerator temperature: the samples were brought to The Provincial Hospital on the same day. Cultures were checked at 1, 2 and 7 days and S. typhi identified by established biochemical and serologic assays at the Microbiology Laboratory, The Provincial Hospital and by Dr. Vee Gill, Clinical Microbiology, NIH. All isolates were also verified for Vi by the antiserum agar technique at the NICHD: there was no discrepancy among the three laboratories. [81].

No additional cases of typhoid fever in the participants were found in the bacteriologic records of The Provincial Hospital and the District Hospital, adjacent to the south part of the Cao Lanh District. The study was closed on May 31, 2000, 27 months after the first injection.

Immunogenicity and Persistence of Vi-rEPA-induced IgG anti-Vi

Paired sera were obtained from 76 participants before the first and 4 weeks after the second injection. To evaluate the duration of vaccine-induced anti-Vi, a 2 mL blood sample was taken at random from 4 vaccinees of each commune each month after the second injection. Serum IgG Vi antibodies were assayed by ELISA as described and expressed in ELISA units (EU). [79].

Statistical Analysis

Vaccine efficacy is expressed as proportionate reduction of cases of typhoid fever: 1−(attack rate in recipients of Vi-rEPA/attack rate in placebo group)×100%. Confidence limits were calculated by the method of Miettinen and Nurminen. [82]. Chi Square, or where appropriate, the Fisher exact test were used for comparison of categorical variables. Logarithms of the antibody concentrations were used in all calculations. Antibody levels were expressed as the geometric mean (G.M.) with 25th and 75th centiles. Comparisons of G.M. were performed with the unpaired t test or paired t test.

Results

Characteristics of the Vaccinees (Table 7)

A total of 12,008 children received at least 1 injection: 11,091 (92.4%) received 2 injections (5,525 Vi-rEPA and 5,566 placebo), 771 (6.4%) received 1 injection (388 Vi-rEPA and 383 placebo) and 146 (1.2%) were injected from a vial with an incorrect code (78 Vi-rEPA and 68 placebo). The sex, age at vaccination, household composition and size, and interval between the two injections were similar between the vaccine groups. The interval between the 2 injections ranged from 28 to 57 days (median 42).

TABLE 7

Characteristics of participants in the Vi-rEPA and placebo groups

| Characteristics | Vi-rEPA | (n = 5, 991) | Placebo | (n = 6, 017) |
|---|---|---|---|---|
| Male | 3,033 | 50.6% | 3,120 | 51.9% |
| Received two injections | 5,525 | | 5,566 | |
| Received only one injection | 388 | | 383 | |

TABLE 7-continued

Characteristics of participants in the Vi-rEPA and placebo groups

| Characteristics | Vi-rEPA | (n = 5, 991) | Placebo | (n = 6, 017) |
|---|---|---|---|---|
| Received incorrect injection | 78 | | 68 | |
| Number of households | 5,076 | | 5,082 | |
| Adults > 18 years/household | 2.89 | | 2.94 | |
| Children ≦ 18 years/household | 2.74 | | 2.76 | |
| Age at vaccination | | | | |
| 2 years | 1,338 | 22.3% | 1,356 | 22.5% |
| 3 years | 1,422 | 23.7% | 1,418 | 23.6% |
| 4 years | 1,628 | 27.2% | 1,597 | 26.5% |
| 5 years | 1,603 | 26.8% | 1,646 | 27.4% |
| Days between the two injections | | | | |
| Median (range) | 42.0 | (29–57) | 42.0 | (28–56) |

Adverse Reactions (Table 8)

Serious side reactions were not noted. The reactions from all intervals after injection (20 minutes, 6, 24, 48 hours) were combined. After the first injection, 113 participants had a temperature of ≧37.5° C.: 81 recipients of Vi-rEPA vs 32 recipients of placebo (p<0.001). Of recipients with a temperature of ≧39.0° C., 17 were injected with Vi-rEPA and 5 with placebo (p=0.01). None of the recipients had ≧5 cm of erythema or swelling.

After the second injection, a temperature of ≧37.5° C. was recorded for 109 recipients of Vi-rEPA and for 25 recipients of placebo (p<0.001). One recipient of Vi-rEPA and one of placebo had a temperature ≧39.0° C. Swelling ≧5 cm was noted in 20 recipients of Vi-rEPA compared to 1 in the placebo group (p<0.001). Erythema ≧5 cm without swelling was noted in 2 recipients of Vi-rEPA and none in the placebo group.

None of these reactions persisted for more than 48 hours after injection.

Among children who received 2 injections from vials with correctly allocated vials (fully vaccinated), there were 4 cases of typhoid fever in the Vi-rEPA group and in the placebo group 47 (efficacy 91.5%, 95% C.I. 77.1–96.6). One additional patient received two injections of placebo from vials with an incorrectly allocated code.

Of children that received only 1 injection, there was 1 case of typhoid fever 42 days after injection of Vi-rEPA and 8 cases throughout the study period in the placebo group. Combining all the cases of typhoid fever, there were 5 in the Vi-rEPA group and 56 in the placebo group (efficacy 91.0%, 95% C.I. 78.6–96.5). The cases in both the Vi-rEPA and placebo groups were distributed evenly among the two to five year-olds. There were two cases during the first year and three cases during the second year after vaccination in the Vi-rEPA group.

Among all cases of typhoid fever, 21 (34%) were hospitalized for an average of 13 days (median 12, range 7 to 24): all were in the placebo group (015 vs 21/56, NS).

TABLE 8

Local reactions and fever following the first and second injections of Vi-rEPA and the placebo (saline).

| | First injection | | | | Second injection | | | | |
|---|---|---|---|---|---|---|---|---|---|
| | Vi-rEPA | | Placebo | | | V-rEPA | | Placebo | |
| | n = | | n = | | p = | n = | | n = | | p = |
| Fever ≧ 37.5° C. | 81 | 1.36% | 32 | 0.54% | <0.001 | 109 | 1.93% | 25 | 0.44% | <0.001 |
| Fever ≧ 39.0° C. | 17 | 0.29% | 5 | 0.08% | 0.01 | 1 | 0.02% | 1 | 0.02 | NS |
| Swelling ≧ 5 cm | 0 | | 0 | | | 20 | 0.35% | 1 | 0.02% | <0.001 |
| Erythema ≧ 5 cm | 0 | | 0 | | | 2 | 0.04% | 0 | | NS |

Following injection, the axillary temperatures of the children were taken and the injection sites inspected for redness and swelling at 6, 24 and 48 hours by a community health worker. The reactions at the intervals were combined.
Efficacy (Table 9)

During the surveillance period (March 8, 1998 through May 31, 2000), 2,335 blood cultures were obtained: 1,121 from recipients of Vi-rEPA and 1,214 from recipients of the placebo. S. typhi was isolated from 61 recipients representing all communes (34 males and 27 females). The number of typhoid fever cases in each commune ranged from 1 to 9 (median 4).

A total of 339 vaccinees (165 Vi-rEPA and 174 placebo) were lost to follow-up (2.8%): 308 moved out of the study area, 2 withdrew from the study and 29 died (12 Vi-rEPA vs 17 placebo) due to drowning (19), dengue fever (3), pneumonia (2), Stevens Johnson Syndrome (2), and 1 each of burns, foreign body in airway, and leukemia. No death was attributed to the vaccination or to typhoid fever.

There were four isolates of Salmonella paratyphi A: 1 received Vi-rEPA and 3 received placebo.

TABLE 9

Efficacy of Vi-rEPA conjugate vaccine against typhoid fever in fully vaccinated children and in those that received only 1 injection: Dong Thap Province, Vietnam, March 8, 1998 through May 31, 2000

| Group | Vi-rEPA | Placebo | Efficacy | (95% C.I.) |
|---|---|---|---|---|
| Fully vaccinated (n =) | 5,525 | 5,566 | | |
| Typhoid fever (n =) | 4 | 47 | 91.5% | (77.1–96.6) |
| Attack rate (cases/10³) | 0.72 | 8.44 | | |
| All participants* (n =) | 5,991 | 6,017 | | |
| Typhoid fever (n =) | 5 | 56 | 91.0% | (78.6–96.5) |
| Attack rate (case/10³) | 0.84 | 9.31 | | |

Characteristics of all typhoid fever patients

| | Vi-rEPA | | Placebo | | |
|---|---|---|---|---|---|
| Male | 5 | (100%) | 29 | (52%) | NS |
| Female | 0 | (0%) | 27 | (48%) | |
| Age at vaccination (years) | | | | | |
| 2 | 2 | (40%) | 16 | (29%) | NS |
| 3 | 1 | (20%) | 17 | (13%) | |
| 4 | 0 | (0%) | 16 | (29%) | |
| 5 | 2 | (40%) | 17 | (30%) | |
| Time period of isolation *of S. typhi* | | | | | |
| 3/98–2/99 (12 months) | 2 | (40%) | 33 | (59%) | NS |
| 3/99–5/00 (15 months) | 3 | (60%) | 23 | (41%) | |

*Includes 1 case who received 2 injections of placebo from an incorrectly allocated vial.
Among those who received only 1 injection, 1 case of typhoid fever occurred 42 days after injection of Vi-rEPA and 8 cases from 25 days to 1 year after injection of placebo.

Serum Levels of IgG Vi Antibodies Before the First and 4 Weeks After the Second Injection (Table 10)

A total of 76 paired sera were available from participants bled before their first and 4 weeks after their second injection. There was no significant difference among the pre-first injection levels of IgG anti-Vi in the two groups and the post-4 week immunization level in recipients of the placebo. Vi-rEPA, in contrast, elicited approximately a 660-fold increase in IgG anti-Vi (p<0.0001): 100% of the recipients of Vi-rEPA had 210-fold rise.

TABLE 10

Serum anti-Vi IgG of participants before their first injection and four weeks after their second injection by age at vaccination

| | | ELISA units | |
|---|---|---|---|
| Vaccine | | [Geometric mean (25th to 75th centiles)] | |
| Group | n = | Pre-1st injection | 4 weeks post 2nd injection |
| Vi-rEPA (all) | 36 | 0.11 (0.06–0.18) | 72.9 (50.7–124) |
| 2–3 years | 13 | 0.10 (0.06–0.12) | 69.0 (56.0–186) |
| 4–5 years | 23 | 0.13 (0.07–0.26) | 75.2 (46.9–124) |
| Placebo (all) | 40 | 0.15 (0.06–0.19) | 0.27 (0.08–0.55) |
| 2–3 years | 13 | 0.13 (0.07–0.20) | 0.13 (0.07–0.14) |
| 4–5 years | 23 | 0.16 (0.07–0.20) | 0.40 (0.09–1.39) |

72.9 vs 0.27, 0.11: p = 0.0001, 75.2 vs 72.9 vs 69.0, NS

Serum IgG anti-Vi was assayed as described in Example 5 herein. [79]. Study participants were injected with the coded vials two times six weeks apart. Blood samples were taken prior to their first injection and 4 weeks after the second injection. 100% of the recipients of Vi-rEPA had ≧10-fold rise of their serum IgG anti-Vi.

Persistence of Vi-rEPA-induced anti-Vi (Table 11)

Blood samples, from 4 randomly selected recipients of each commune, were taken each month: only those at 4 intervals (0, 6 months, 1 and 2 years) are shown in Table 5. The pre-immunization IgG anti-Vi levels of the Vi-rEPA and placebo groups were similar. At 6 months following the second injection, the IgG anti-Vi levels in the recipients of Vi-rEPA were 22.5 EU or 35-fold higher than those of the placebo group (p<0.001). At 2 years, Vi-rEPA-induced IgG anti-Vi levels decreased approximately 2.1 fold from those at 6 months to 10.7 EU: this level was 18.8-fold higher than the controls (10.7 vs 0.57, p<0.001).

There was a slight rise of the placebo group from 0.15 EU to 0.57 (NS).

A tendency for an age-related immunogenicity and persistence of IgG anti-Vi was observed when the vaccinees were stratified by age into two to three year-olds and four to five-year-olds. The four to five year-olds had a higher level of IgG anti-Vi at all three post-immunization intervals. The decline of IgG anti-Vi levels from 6 months to 2 years was less in the 4 to 5-year-olds (1.4-fold) compared to the 2 to 3-year-olds (2.4-fold) (NS).

TABLE 11

Persistence of serum IgG anti-Vi in fully vaccinated children by age at vaccination stratified into 2–3 and 4–5 year-old age groups

| | ELISA units (Geometric mean, 25th to 75th centiles) | | | |
|---|---|---|---|---|
| Vaccine | Interval after immunization | | | |
| group | Pre- | 6 months | 1 year | 2 years |
| Vi-rEPA (all) | 0.12 (0.06–0.20) | 22.5 (13.8–47.3) | 18.7 (10.3–32.6) | 10.7 (6.4–24.8) |
| 2–3 years | 0.12 (0.05–0.23) | 18.6 (13.1–47.3) | 14.3 (7.1–18.6) | 7.6 (6.2–17.4) |
| 4–5 years | 0.13 (0.07–0.20) | 25.1 (13.8–49.0) | 21.4 (14.0–37.5) | 18.4 (8.2–41.4) |
| Placebo (all) | 0.15 (0.06–0.25) | 0.65 (0.28–1.03) | 0.31 (0.17–0.52) | 0.57 (0.15–2.50) |
| 2–3 years | 0.10 (0.05–0.18) | 0.50 (0.27–0.51) | 0.30 (0.15–0.38) | 0.70 (0.26–1.13) |

TABLE 11-continued

Persistence of serum IgG anti-Vi in fully vaccinated children by age at vaccination stratified into 2–3 and 4–5 year-old age groups

| Vaccine group | ELISA units (Geometric mean, 25th to 75th centiles) Interval after immunization | | | |
|---|---|---|---|---|
| | Pre- | 6 months | 1 year | 2 years |
| 4–5 years | 0.20 (0.07–0.59) | 1.00 (0.33–1.72) | 0.30 (0.17–0.59) | 0.50 (0.15–2.50) |
| | 10.7 vs 0.57, p < 0.001; 18.4 vs 10.7 vs 7.6, NS | | | |

A blood sample was taken at random from 4 participants at each of the 16 communes every month for 24 months.
Only the G.M. serum IgG anti-levels at the 0, 6 months and 1 and 2 years intervals are shown above.

The 3rd year antibody persistent levels for the phase II Vi-rEPA conjugate study are as follows:

| ELISA units [Geometric mean (25th to 75th centiles)] | | | |
|---|---|---|---|
| Adults(n = 20) | 5–14 yr old (n = 8) | 2–4 yr old (1 inj, n = 28) (2 inj, n = 28) | |
| 92.64 | 4.80 | 4.83 | 4.56 |

Levels of Serum IgG anti-Vi from Patients.

Only 3 sera from the 4 blood samples drawn for culture from the fully vaccinated patients (recipients of Vi-rEPA) were available: their levels were 4.76, 14.6 and 40.3 EU. There were 37 sera from typhoid fever cases in the placebo group whose IgG anti-Vi levels ranged from 0.05 EU to 3.7 in 36 sera, G.M. 0.41 EU: one patient in the placebo group had 85.8 EU.

Discussion of Efficacy Trial

Two novel observations from this trial merit emphasis. One is that the efficacy for Vi-rEPA (approximately 91.5%) is the highest reported for any typhoid vaccine. The other is the demonstration of the efficacy of a typhoid vaccine, for the first time, in young children. A high degree of efficacy was predicted by the immunogenicity of Vi-rEPA in 2–4 year-olds compared to that of Vi in adults and in 5–14 year-olds. [Example 5 herein, 79]. Since it is the level of serum IgG anti-Vi induced by a Vi-based vaccine that determines its efficacy, we predict that Vi-rEPA will be at least as effective in older children and adults as it was shown to be for the 2–5 year-olds. [47]. We are conducting passive surveillance of the participants for the next two years to evaluate the duration of protection and persistence of IgG anti-Vi induced by Vi-rEPA.

Vi-rEPA was safe. We subtracted the number of reactions in the placebo group from that of the Vi-rEPA recipients for each category. After the first injection 0.9% of the vaccinees had a temperature ≧37.5° C. and 0.2% had ≧39.0° C. attributable to Vi-rEPA.

After the second injection, swelling ≧5 cm at the injection site was observed in 20 of Vi-rEPA recipients compared to 1 in the placebo group. Fever attributable to Vi-rEPA occurred in 1.4% who had temperature ≧37.5° C. but none had ≧39.0° C. This degree of safety was observed in our Phase 2 trial of Vi-rEPA and could be predicted by the observation that Vi-rEPA met the Requirements of the World Health Organization for Vi polysaccharide vaccine. [Example 5 herein, 79, 80].

Although the numbers are not statistically significant there is a suggestion that patients who received 1 or 2 injections of Vi-rEPA and who developed typhoid fever (n=5) had a milder course than the controls (n=56) because 21 of latter (37.5%) were hospitalized compared to none of the former. We speculate that the higher levels of IgG anti-Vi in typhoid fever cases vaccinated with Vi-rEPA compared to those injected with placebo could explain this milder course of disease. The higher to levels of IgG anti-Vi in these patients is likely mediated by a T-cell primed B-cell population induced by the Vi-rEPA.

There was a comparable number of blood cultures taken from recipients of Vi-rEPA (n=121 1) and of placebo (n=1214). S. typhi isolated from the placebo group (56/1214) represents 4.6% children with ≧3 days of fever. But the diagnosis of typhoid fever by the results of a single blood culture is not efficient. [13, 83, 84]. It is estimated that only approximately 50% of typhoid fever cases are identified by this technique compared to culture of the bone marrow. In addition, the yield of S. typhi from blood cultures is related to the duration of fever. For example, in our epidemiologic investigation of typhoid fever in this study area, we found that the yield of S. typhi from blood cultures from children after 3 days of fever was 4.6% compared to 17% from those with ≧7 days of fever. [73]

The unusual structure, molecular size, and physicochemical properties of Vi contributed to the laborious development of Vi-rEPA. [31, 47, 51, 52, 53, 54, 79]. Both the safety and immunogenicity of Vi-rEPA in this trial were comparable to those of a similar product evaluated in Phase 1 and 2 studies in Vietnam indicating consistency in the production of this new vaccine. [Example 5 herein, 79]. Vi-rEPA-induced levels of IgG anti-Vi declined approximately 2-fold in the ensuing 2 years but there was no change in the efficacy of the vaccine. Based upon the level in the 2–3 year-olds at the 2 year interval after vaccination with Vi-rEPA, we propose that IgG anti-Vi of no more than 8 EU is the minimal protective level. [85]

Our objective is to provide a safe and effective typhoid fever vaccine for routine vaccination of infants. Accordingly, we plan an evaluation of the immunogenicity of Vi-rEPA when administered with DTP. Should Vi-rEPA elicit levels of anti-Vi in infants comparable to those in the 2 to 5 year-olds, this new typhoid vaccine could be administered as part of the WHO Expanded Program on Immunization. [24]. In addition, Vi-rEPA can be predicted to be a highly effective vaccine for the military and travelers to areas with high rates of typhoid fever. [65].

Summary of Efficacy Trial

Background Typhoid fever is common and serious in developing countries. Licensed vaccines for typhoid fever confer only about 70% immunity, do not protect young children and are not used for routine vaccination. A newly developed conjugate of *Salmonella typhi* Vi polysaccharide, bound to a mutant nontoxic *Pseudomonas aeruginosa* exotoxin A (rEPA), demonstrated enhanced immunogenicity in adults, 5–14 and 2–4 year-olds.

Methods In a double-blinded, placebo-controlled, randomized trial, the safety and efficacy of Vi-rEPA was evaluated in 2–5 year-olds of 16 communes in Dong Thap Province, Mekong Delta, Vietnam. Participants (11,091) received 2 injections 6 weeks apart of Vi-rEPA or placebo (saline). Typhoid fever was diagnosed by isolation of *S. typhi* from blood cultures after $\geq 3$ days of fever ($\geq 37.5°$ C.) was identified by active surveillance for 27 months. Efficacy was estimated by comparing the attack rate of typhoid fever in recipients of Vi-rEPA to the controls.

Results *S. typhi* was isolated from 4 fully vaccinated recipients of Vi-rEPA compared to 47 of placebo (efficacy 91.5%, 95% C.I. 77.1–96.6). Cases were distributed evenly by age and throughout the study. Among recipients of only 1 injection, there was 1 case in the Vi-rEPA group and 8 in the placebo group. Serious side reactions were not observed.

Conclusions Vi-rEPA was safe, immunogenic and elicited $\geq 90\%$ efficacy in 2 to 5 year-olds. The high level of serum IgG Vi antibodies and of efficacy in 2–5 year-olds indicate that Vi-rEPA will be at least as protective in older individuals including travelers and the military.

References

1. Acharya, I. L., Lowe, C. U., Thapa, R., Gurubacharya, V. L., Shrestha, M. B., Bryla, D. A., Cramton, T., Trolifors, B., Cadoz, M., Schulz, D., Armand, J., Schneerson, R., and Robbins, J. B. 1987. Prevention of typhoid fever in Nepal with the Vi capsular polysaccharide of *Salmonella typhi*: A preliminary report one year after immunization. N. Engl. J. Med. 317:1101–1104
2. Blaser, M. J., R. Newman. 1982. A review of human salmonellosis: I. Infective dose. Rev. Infect. Dis. 4:1096–1106
3. Bodhidatta, L., D. N. Taylor, U. Thisyakom, and P. Echeverria. 1987. Control of typhoid fever in Bangkok, Thailand, by annual immunization of school children with parenteral typhoid vaccine. Rev. Infect. Dis.9:841–845
4. Bradford M M. A rapid and sensitive method for the quantitation of microgram quantities of protein utilizing the principle of protein-dye binding. Anal Biochem 1976;72:248–254
5. Brugier, J-C, A. Barra, D. Schulz, J-L. Preud'homme. 1993. Isotypes of human vaccinal antibodies to the Vi capsular polsyaccharide of *Salmonella typhi*. Int. J. Clin. Lab. Res. 23:38–41
6. Cameron D M, R J Collier. 1987. Exotoxin A of *Pseudomonas aeruginosa*: substitution of glutamic acid 553 with aspartic acid drastically reduces toxicity and enzymatic activity. J. Bacteriol. 169:4967–4971
7. Fass R, van de Walle M, Shiloach A, Joslyn A, Kaufman J, Shiloach J. Use of high density cultures of *Escherichia coli* for high level production of recombinant *Pseudomonas aeruginosa* exotoxin A. Appl Microbiol Biotechnol 1991;36:65–69
8. (a) Chu, C-Y, R. Schneerson, J. B. Robbins, S. C. Rastogi. 1983. Further studies on immunogenicity of *Haemophilus influenzae* type b and pneumococcal 6A polysaccharide-protein conjugates. Infect Immun 40:245–256; (b) C. Chu, et al. 1991. Infect. Immun., 59:4450–4458.
9. Fattom, A., Vann, W. F., Szu, S. C., Sutton, A., Li, X., Bryla, D., Schiffman, G., Robbins, J. B., and Schneerson, R. 1988. Synthesis and physiochemical and immunological characterization of pneumococcus type 12F polysaccharide-diptheria toxoid conjugates. Infect. Immun. 56:2292–2298
10. Fattom, A., J. Shiloach, D. A. Bryla, D. Fitzgerald, I. Pastan, W. W. Karakawa, J. B. Robbins, R. Schneerson. 1992. Comparative immunogenicity of conjugates composed of the *Staphylococcus aureus* type 8 capsular polysaccharide bound to carrier proteins by adipic acid dihydrazide or N-succinimidyl-3-(2-pyridyldithio) propionate. Infect. Immun. 60:584–589
11. Field R. Biochem J 1971;124:581–590
12. Gaines, S., J. A. Currie, and J. G. Tully. 1960. Production of incomplete Vi antibody in mice. Proc. Soc. Exp. Biol. Med. 104:602–605.
13. Gilman, R. H., M. Terminel, M. M. Levine, P. Hernandez-Mendoza, R. B. Hornick. 1975. Relative efficacy of blood, urine, rectal swab, bone-marrow, and rose-spot cultures for recovery of *Salmonella typhi* in typhoid fever. Lancet. i:1211–1213
14. Gotschlich, E. C., M. Rey, W. R. Sanborn, R. Triau and B. Cvjetanovic. 1972. The immunological responses observed in field studies in Africa with Group A meningococcal vaccines. Progress in Immunobiological Stand. 129:485–491.
15. World Health, Organization Expert Committee on Biological Standardization. 1977. Technical Report Series, 610. WHO, Geneva, Switzerland.
16. Jacobson, B S and K R Fairman. 1980. A colorimetric assay for carbodiimides commonly used in peptide synthesis and carboxyl group modification. Anal Biochem 106, 114.
17. Johansson, H. J., C. Jägersten, and J. Shiloach. 1996. Large scale recovery and purification of periplasmic protein from *E. coli* using explanded bed adsorption chromatograhy followed by new ion exchange media. J. Biotech. 48:9–14.
18. Kim, Y-R., J-H. Yoo, J-K. Hur, J. H. Kang, W-S. Shin, M-W. Kang. 1995. Immunogenicity of Vi capsular polysaccharide vaccine evaluated for 3 years in Korea. K Korean Med. Sci. 10:314–317
19. Heidelberger, M., M. M. DiLapi, M. Siegel and A. W. Walter. 1950. Persistance of antibodies in human subjects injected with pneumococcal polysaccharides. J. Immunol. 65:535–541
20. Hestrin S. The reaction of acetylcholine and other carboxylic acid derivatives with hydroxylamine, and its analytical application. J Biol Chem 1949;180:249–2261
21. Hien, T. T., D. B. Bethell, N. T. T. Hoa, J. Wain, T. S. Diep, L. T. Phi, B. M. Cuong, N. M. Duong, P. T. Thanh, A. L. Walsh, N. P. J. Day and N. J. White. 1995. Short course of Ofloxacin for treatment of multidrug-resistant typhoid. Clin. Infect. Dis. 20:915–923
22. Hochstein, H. D. 1990. Role of the FDA in regulating the Limulus amoebocyte lysate tests, p. 38–49. In R. B. Prior (ed). Clinical application of the Limulus amoebocyte lysate test. CRC Press, Inc., Boca Raton, Fla.
23. Hornick, R. B., S. E. Greisman, T. E. Woodward, H. L. DuPont, A. T. Dawkins, and M. J. Snyder. 1970. Typhoid fever: pathogenesis and immunologic control. (second of two parts) N. Eng. J. Med. 283:739–746
24. Ivanoff, B., M. M. Levine and P. H. Lambert. 1994. Vaccination against typhoid fever: Present status. Bull. W. H. O. 72:957–971
25. Jacobson B S, Fairman K R. A colorimetric assay for carbodiimides commonly used in peptide synthesis and carboxyl group modification. Anal Biochem 1980;106:114–117

26. Kawata, Y. 1970. A study of the molecular types of immunoglobulin. II. Mouse protection study of Vi antibody against typhoid infection. Acta Medicine Univ. Kioto. 40:284–290
27. Keitel W A, Bond N L, Zahradnik J M, Cramton T A, Robbins J B. Clinical and serological responses following primary and booster immunization with *Salmonella typhi* Vi capsular polysaccharide vaccines. Vaccine 1994;12: 195–199
28. Kim, Y. R., J. H. Yoo, J. K. Hur, J. H. Kang, W. S. Shin, M. W. Kang. 1995. Immunogenicity of Vi capsular polysaccharide vaccine evaluated for three years in Korea. J. Korean Med. Sci. 10:314–317
29. Klugman, K. P., Gilbertson, I. T., Koornhof, H. J., Robbins, J. B., Schneerson, R., Schulz, D., Cadoz, M., Armand, J., and Vaccine Advisory Committee. 1987. Protective activity of Vi capsular polysaccharide vaccine against typhoid fever. Lancet ii:1165–1169
30. Klugman, K. P., H. J. Koornhof, J. B. Robbins, N. M. LeCam. 1996. Immunogenicity, efficacy and serological correlate of protection of *Salmonella typhi* Vi capsular polysaccharide vaccine three years after immunization. Vaccine 14:435–438
31. Kossaczka, Z., Bystricky, S., Bryla, D. A., Shiloach, J., Robbins, J. B., and Szu, S. C. 1997. Synthesis and immmunological properties of Vi and di-o-acetyl pectin conjugates with adipic acid dihydrazide as the linker. Infect. Immun. 65:2088–2093
32. Kumate, J., J. L. Penaloza and A. Llausas. 1974. La fiebre tifoidea en el primer ano de la vida. Bol. Med. Hosp. Infant Mex. 31:925–932
33. Landy, M. 1954. Studies in Vi antigen. VI. immunization of human beings with purified Vi antigen. Amer. J. Hyg. 60:52–62.
34. Landy, M., A. G. Johnson and M. E. Webster. 1961. Studies on Vi antigen. VIII. Role of acetyl in antigenic activity. Amer. J. Hyg. 73:55–65
35. Landy, M., S. Gaines, J. R. Seal, and J. E. Whiteside. 1954. Antibody responses of man to three types of antityphoid immunizing agents: Heat-phenol fluid vaccine, acetone-dehydrated vaccine and isolated Vi and O antigens. Amer. J. Publ. Hlth. 44:1572–1579.
36. Levin, D. M., K-H Wong, H. Y. Reynolds, A. Sutton, and R. S. Northrup. 1975. Vi antigen fron *Salmonella typhosa* and immunity against typhoid fever. 11. Safety and antigenicity in humans. Infect. Immun. 12:1290–1294
37. Lukac M, G B Pier, R J Collier. Toxoid of *Pseudomonas aeruginosa* exotoxin A generated by deletion of an active-site residue. Infect Immun 1988;56:3095–3098
38. Murphy, J. R., L. Grez, L. Schlesinger, C. Ferreccio, S. Baqar, C. Munoz, S. S. Wasserman, G. Losonsky, J. G. Olson, M. M. Levine. Immunogenicity of *Salmonella typhi* Ty21a vaccine for young children. Infect. Immun. 59:4291–4298
39. Monsigny M, et al. Colorimetric determination of neutral sugars by a resorcinol sulfuric acid micromethod. Anal Biochem 1988;175:525–530
40. Mirza, N. B., I. A. Wamola, B. A. Estambale, E. Mbithi, M. Pollet. 1995. Typhim Vi vaccine against typhoid fever: a clinical trial in Kenya. East Afr. 72:162–164
41. Muschel, L. H. and H. P. Treffers. 1956. Quantitative studies on the bactericidal actions of serum and complement. III. Observations on sera obtained after T.A.B. vaccination or during tyhoid fever. J. Immunol. 76:20–27.
42. Nguyen, T. A., H. B. Khiem, N. T. Dung. 1993. Le fievre typhoid au sud VietNam, 1990–1993. Bull. Soc. Path. Ex. 86:476–478
43. Pittman, M. and H. J. Bohner. 1966. Laboratory assays of different types of field trial typhoid vaccines and relationship to efficacy in man. J. Bacteriol. 91:1713–1723.
44. Qadri, A. 1997. Identification of specific recognition molecules on murine mononuclear phagocytes and B lymphocytes for Vi capsular polysaccharide: modulation of MHC class II expression on stimulation with the polysaccharide. Immunology 92:146–152
45. Robbins, J. D., and Robbins, J. B. 1984. Re-examination of the immunopathogenic role of the capsular polysaccharide (Vi antigen) of *Salmonella typhi*. J. Infect. Dis. 150:436–449.
46. Robbins, J. B., and Schneerson, R.: Polysaccharide-protein conjugates: A new generation of vaccines. J. Infect. Dis. 161:821–832, 1990.
47. Robbins, J. B., Schneerson, R., and Szu, S. C.: Perspective: Hypothesis: Serum IgG antibody is sufficient to confer protection against infectious diseases by inactivating the inoculum. J. Infect. Dis. 171:1387–1398, 1995.
48. Rowe, B., L. R. Ward and E. J. Threlfall. 1990. Spread of multiresistant *Salmonella typhi*. Lancet 336:1065
49. Saha, S. K., S. K. Saha. 1994. Antibiotic resistance of *Salmonella typhi* in Bangladesh. J. Antimicrob. Chemother. 33:190–191
50. Schneerson, R., Barrera, O., Sutton, A., and Robbins, J. B. 1980. Preparation, characterization and immunogenicity of Haemophilus influenzae type b polysaccharide-protein conjugates. J. Exp. Med. 152:361–376.
51. Szu, S. C., Stone, A. L., Robbins, J. D., Schneerson, R., and Robbins, J. B.: Vi capsular polysaccharide-protein conjugates for prevention of typhoid fever. J. Exp. Med. 166:1510–1524, 1987.
52. Szu, S. C., Li, X., Schneerson, R., Vickers, J., and Robbins, J. B.: Comparative immunogenicities of Vi polysaccharide-protein conjugates composed of cholera toxin or its B-subunit as a carrier bound to high or lower molecular weight Vi. Infect. Immun. 57:3823–3827, 1989.
53. Szu, S. C., X. Li, A. L. Stone, J. B. Robbins, J. B. 1991. Relation between the structure and immunologic properties of the Vi capsular polysaccharide. Infect. Immun. 59:4555–4561.
54. Szu, S. C., D. N. Taylor, A. C. Trofa, J. D. Clements, J. Shiloach, J. C. Sadoff, D. A. Bryla, J. B. Robbins. 1994. Laboratory and preliminary clinical characterization of Vi capsular polysaccharide-protein conjugate vaccines. Infect. Immun. 62:4440–4444.
55. Am, N. T., Khiem, H. B., Dung, N. T. 1993. La fièvre typhoïde au Sud du VietNam, 1990–1993. Bull. Soc. Path. Ex. 86:476–478
56. Wong, K. H., J. C. Feeley, and M. Pittman. 1972. Effect of a Vi-degrading enzyme on potency of typhoid vaccines in mice. J. Infect. Dis. 125:360–366
57. Wong, K. H. and J. Feeley. 1972. Isolation of Vi antigen and a simple method for its measurement. App. Microbiol. 24:628–633
58. Wong, K. H., J. C. Feeley, M. Pittman, and M. E. Forlines. 1974. Adhesion of Vi antigen and toxicity in typhoid vaccines inactivated by acetone or by heat and phenol. J. Infect. Dis. 129:501–506
59. World Health Organization Expert Committee on Biological Standardization. 1977. Technical Report Series, 610. WHO, Geneva, Switzerland.
60. World Health Organization Expert Committee on Biologic Standardization. Technical Report Series 840, 43rd Ed Geneva, Switzerland. Requirements on Vi polysaccharide for typhoid. 1993:14–32.

61. Yoshihiro J, V. K. Chaudhary, T. Kondo, S. Adhya, D. J. Fitzgerald, I. Pastan. 1988. Mutational analysis of domain 1 of Pseudmonas exotoxin. J. Biol. Chem. 263:13203–13207
62. U.S. Pat. No. 5,204.098, Polysaccharide Protein Conjugates, Szu et al.
63. Bhutta Z A, Naqvi S H, Razzaq R A, and Farooqui B J. Multidrug-resistant typhoid in children: presentation and clinical feature. Rev Infect Dis 1991;13:832–6.
64. Wain J, Nguyen T T H, Nguyen T C, et al. Quinolone-resistant Salmonella typhi in Vietnam: Molecular basis of resistance and clinical response to treatment. Clin Infect Dis 1997;25:1404–10.
65. Mermin J H, Townes J M, Gerber M, Dolan N, Miontz E D, Tauxe R V. Typhoid fever in the United States, 1985–1994: changing risks of international travel and increasing antimicrobial resistance. Arch Intern Med 1998; 158:633–8.
66. Mermin J H, Villar R, Carpenter J, et al. A massive epidemic of multi-resistant typhoid fever in Tajikistan associated with consumption of municipal water. J Infect Dis 1999;179:1416–22.
67. Rao P T, Rao K V K. Typhoid fever in children. Indian J Pediatr 1959;26:258–64.
68. Scragg J, Rubidge C, and Wallace H L. Typhoid fever in African and Indian children in Durban. Arch Dis Child 1969;44:18–28
69. Galloway H, Clark N S and Blackhall M. Paediatric aspects of the Aberdeen typhoid outbreak. Arch Dis Child 1986;41:63–8.
70. Thisyakom U, Mansuwan P, Taylor D N. Typhoid and paratyphoid fever in 192 hospitalized children in Thailand. Am J Dis Child 1987;141:862–85.
71. Simanjuntak C R, Paleologo F P, Punjabi N H, et al. Oral immunization against typhoid fever in Indonesia with Ty21a vaccine. Lancet 1991;338:1055–9.
72. Sinha A, Sazawal S, Kumar R, et al. Typhoid fever in chldren aged less than 5 years. Lancet 1999;354:734–7.
73. Lin F Y, Ho V A, Bay P V, et al. The epidemiology of typhoid fever in the Dong Thap Province, Mekong delta region of Vietnam. Am J Trop Med Hyg. Amer J Trop Med Hyg, in press
74. Tarr P E, Kuppin S L, Jones T C, Ivanoff B, Aparain P G, Heymann D C. Consideration regarding mass vaccination against typhoid fever as an adjunct to sanitation and public health measures: potential use in an epidemic in Tajikistan. AmerJ Trop Med 1999:61:163–170.
75. Levine M M, Ferreccio C. Abrego P, Martin O S, Ortiz E, Cryz S. Duration of efficacy pf Ty21a, attentuated Salmonella typhi live oral vaccine. Vaccine 1999;17: Suppl 2: S22–7.
76. Centers for Disease Control and Prevention. Typhoid immunization: recommendations of the Advisory Committee on Immunization Practices. MMWR Morb Mortal Wkly Rep 1994;31:1–7.
77. Felix A, Pitt R M. A new antigen of B. typhosus. Lancet 1934;186–91.
78. Robbins J B, Schneerson R, Anderson P, Smith D H. Prevention of systemic infections, especially meningitis, caused by Haemophilus influenzae type b: Impact on public health and implications for other polysaccharide-based vaccines. JAMA 1996;276:1181–5.
79. Kossaczka Z, Lin F Y, Ho A V, et al. Safety and immunogenicity of Vi conjugate vaccines for typhoid fever in adults, 5 to 14 year-olds, and 2 to 4 year-olds in Vietnam. Infect Immun 1999;67:5806–10.
80. World Health Organization. Annex 1: Requirements for Vi polysaccharide typhoid vaccine (Requirements for Biological Substances No. 48). WHO Technical Report Series 1994; No. 840 15–29.
81. Nolan C M, LaBorde E A, Howell R T, Robbins J B. Identification of Salmonella typhi in faecal specimens by an antiserum agar method. J Med Microbiol 1980;13:373–7.
82. Miettinen O, Nuriminen M. Comparative analysis of two rates. Statistics in Medicine, 1985;4:213–26.
83. Escamilla J, Santiago L T, Uylangco C V, Cross J H. Evaluation of sodium polyanethol sulfonate as a blood culture additive for recovery of Salmonella typhi and Salmonella paratyphi A. J Clin Microbiol 1983;18:380–3
84. Farooqui B J, Khursid M, Ashfaq M K, Khan M A. Comparative yield of Salmonella typhi from blood and bone marrow cultures in patients with fever of unknown origin. J Clin Pathol 1991;44:258–9.
85. Bystricky S, Szu S C. O-acetylation affects the binding properties of the carboxyl groups on the Vi bacterial polysaccharide. Biophy Chem 1994;51:1–7.

What is claimed is:

1. A method of inducing, in a human, serum antibodies which protect against infection with S. typhi, comprising administering to said human, a composition comprising a molecular conjugate of the S. typhi Vi polysaccharide comprising an N-acetyl group and covalently bound through a carboxylic acid dihydrazide linker to Pseudomonas aeruginosa recombinant exoprotein A in a pharmaceutically acceptable carrier.

2. The method of claim 1 wherein said conjugate molecule is administered at a dose of about 3 micrograms to about 50 micrograms of S. typhi Vi polysaccharide.

3. The method of claim 2 wherein said conjugate molecule is administered at a dose of about 25 micrograms of Vi polysaccharide.

4. The method of claim 1 wherein the antibodies protect the human against infection by S. typhi.

5. The method of claim 4 wherein the human is a 2 to 3 year old.

6. The method of claim 4 wherein the human is a 4 to 5 year old.

7. The method of claim 4 wherein the human is a 5 to 17 year old.

8. The method of claim 4 wherein the human is an adult.

9. The method of claim 1 wherein said Vi polysaccharide is covalently bound to the rEPA by means of an adipic acid dihydrazide linker.

10. A method for vaccinating a human against S. typhi infection, comprising administering to the human an immunizing amount of a composition comprising a molecular conjugate of S. typhi Vi polysaccharide comprising an N-acetyl group and covalently bound through a carboxylic dihydrazide linker ofPseudomonas aeruginosa recombinant exoprotein A in a pharmaceutically acceptable carrier.

11. The method of claim 10 wherein the human is a 2 to 3 year old.

12. The method of claim 10 wherein the human is a 4 to 5 year old.

13. The method of claim 10 wherein the human is a 5 to 14 year old.

14. The method of claim wherein the human is an adult.

15. The method of claim 10 wherein the S. typhi Vi polysaccharide is covalently bound to the Pseudomonas aeruginosa recombinant exoprotein A by means of an adipic acid dihydrazide linker.

16. A vaccine composition comprising an immunologically effective amount of a molecular conjugate of S. typhi Vi polysaccharide comprising an N-acetyl group and covalently bound through a carboxylic acid dihydrazide linker to *Pseudomonas aeruginosa* recombinant exoprotein A, in a pharmaceutically acceptable carrier.

17. The vaccine composition of claim 16 wherein the *S. typhi* Vi polysaccharide is covalently bound to the *Pseudomonas aeruginosa* recombinant exoprotein A by means of an adipic acid dihydrazide linker.

18. The vaccine composition of claim 16, wherein the vaccine composition is a human vaccine composition.

19. The vaccine composition of claim 17, wherein the vaccine composition is a human vaccine composition.

* * * * *

UNITED STATES PATENT AND TRADEMARK OFFICE
Certificate

Patent No. 6,797,275 B1                                                Patented: September 28, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Zuzana Kossaczka, Bethesda, MD (US); Shousun Chen Szu, Bethesda, MD (US); John B. Robbins, Chevy Chase, MD (US); Rachel Schneerson, Bethesda, MD (US); and Joseph Shiloach, Rockville, MD (US).

Signed and Sealed this Tenth Day of July 2007.

WILLIAM R. DIXON, JR.
Technology Center 1600